(12) United States Patent
Ghosh et al.

(10) Patent No.: US 9,346,820 B2
(45) Date of Patent: May 24, 2016

(54) HIV-1 PROTEASE INHIBITORS HAVING GEM-DI-FLUORO BICYCLIC P2-LIGANDS

(71) Applicant: Purdue Research Foundation, West Lafayette, IN (US)

(72) Inventors: Arun K. Ghosh, West Lafayette, IN (US); Hiroaki Mitsuya, Kumamoto (JP); Sofiya Yashchuk, Hoffman Estates, IL (US)

(73) Assignee: Purdue Research Foundation, West Lafayette, IN (US)

(*) Notice: Subject to any disclaimer, the term of this patent is extended or adjusted under 35 U.S.C. 154(b) by 2 days.

(21) Appl. No.: 14/483,043

(22) Filed: Sep. 10, 2014

(65) Prior Publication Data
US 2015/0072958 A1  Mar. 12, 2015

Related U.S. Application Data

(60) Provisional application No. 61/876,474, filed on Sep. 11, 2013.

(51) Int. Cl.
*C07D 493/04* (2006.01)

(52) U.S. Cl.
CPC .................................. *C07D 493/04* (2013.01)

(58) Field of Classification Search
CPC ................................................... C07D 493/04
USPC ............... 514/158, 321, 367, 375, 456, 470; 546/198; 548/159, 222; 549/396, 464
See application file for complete search history.

(56) References Cited

U.S. PATENT DOCUMENTS 7,700,645 B2* 4/2010 Vermeersch et al. .......... 514/456

OTHER PUBLICATIONS

Exhibit I p. 1 (2015).*
Exhibit II p. 1 (2015).*
Ghosh and Anderson "Tetrahydrofuran, tetrahydropyran ..." Future Med. Chem. 3(9)1181-1197 (2011).*
Patani et al. "Bioisosterism ..." Chem. Rev. v.96, p. 3147-76 (1996).*
Amano, et al., "A Novel Bis-Tetrahydrofuranylurethane-containing Nonpeptidic Protease Inhibitor (PI), GRL-98065, is Potent against Multiple-PI-Resistant Human Immunodeficiency Virus In Vitro", Antimicrobial Agents and Chemotherapy, vol. 51. No. 6, (2007), 2143-2155.
Bright, Tara V, et al., "A convenient chemical-microbial method for developing fluorinated pharmaceuticals", Organic and Biomolecular Chemistry, 11(7):, (2013), 1135-1142.
Ghosh, Arun K, et al., "The development of cyclic sulfolanes as novel and high-affinity P2 ligands for HIV-1 protease inhibitors.", Journal of Medicinal Chemistry 37(8), (1993), 2300-2310.

(Continued)

*Primary Examiner* — Celia Chang
(74) *Attorney, Agent, or Firm* — Schwegman Lundberg & Woessner, P.A.

(57) ABSTRACT

Various embodiments of the present invention relate to, among other things, compounds and methods of using those compounds to treat an HIV infection. The compounds of the various embodiments of the present invention provide, among other things, therapeutic agents having enhanced penetration capability across the blood-brain barrier, such that they can enter the CNS to treat an HIV-1 infection in the CNS.

15 Claims, 5 Drawing Sheets

Structures of GRL-04810, GRL-05010 and darunavir

(56) References Cited

OTHER PUBLICATIONS

Ide, Kazuhiko, et al., "Novel HIV-1 protease inhibitors (PIs) containing a bicyclic P2 functional moiety, tetrahydropyrano-tetrahydrofuran, that are potent against multi-PI-resistant HIV-1 variants", Journal of American Society for Microbiology: Antimircobial Agents and Chemotherapy 55(4), (2011), 1717-1727.

Karppi, Jouni, et al., "Adsorption of drugs onto a pH responsive poly (N,N-dimethyl aminoethyl methacrylate) grafted anion-exchange membrane in vitro", International Journal of Pharmaceutics 338, (2007), 7-14.

Koh, Yasuhiro, et al., "In Vitro Selection of Highly Darunavir-Resistant and Replication-Competent HIV-1 Variants by Using a Mixture of Clinical HIV-1 Isolates Resistant to Multiple Conventional Protease Inhibitors", Journal of Virology 82(22), (2010), 11961-11969.

Liu, Peng, et al., "Fluorinated Nucleosides: Synthesis and biological implication", Journal of Fluorine Chemistry 129(9), (2008), 743-766.

Nakagawa, Shinsuke, et al., "A new blood—brain barrier model using primary rat brain endothelial cells, pericytes and astrocytes", Journal of Neurochemistry International 54(3-4), (2009), 253-263.

Nakagawa, Shinsuke, et al., "Pericytes from brain microvessels strengthen the barrier integrity in primary cultures of rat brain endothelial cells.", Journal of Cellular and Molecular Neurobiology 27(6), (2007), 687-694.

Rak, Jakub, et al., "On the Solubility and Lipophilicity of Metallacarborane Pharmacophores", Journal of Molecular Pharmaceutics 10(1), (2013), 1751-1759.

Surleraux, Dominique L.N.G, et al., "Design of HIV-1 Protease Inhibitors Active on Multidrug-Resistant Virus", Journal of Medicinal Chemistry 48(6), (2005), 1965-1973.

Tojo, Yasushi, et al., "Novel Protease Inhibitors (PIs) Containing Macrocyclic Components and 3(R),3a(S),6a(R)-bis-Tetrahydrofuranylurethane (bis-THF) That Are Potent Against Multi-PI-Resistant HIV-1 Variants In Vitro", Antimicrobial Agents and Chemotherapy 54(8), (2010), 3460-3470.

Yang, Yan-Yan, et al., "Synthesis of 3',3'-Difluoro-2'-hydroxymethyl-4',5'-Unsaturated Carbocyclic Nucleosides", Journal of Organic Letters 9(26), (2007), 5437-5440.

Yoshimura, Kazuhisa, et al., "A Potent Human Immunodeficiency Virus Type 1 Protease Inhibitor, UIC-94003 (TMC-126), and Selection of a Novel (A28S) Mutation in the Protease Active Site", Journal of Virology, vol. 76(3), (2002), 1349-1358.

* cited by examiner

Figure 6. Structural interactions of GRL-04810 and GRL-05010 with HIV-1 protease.

HIV-1 PROTEASE INHIBITORS HAVING GEM-DI-FLUORO BICYCLIC P2-LIGANDS

CROSS-REFERENCE TO RELATED APPLICATIONS

This application claims priority to U.S. Provisional Appl. Ser. No. 61/876,474, filed 11 Sep. 2013, the entire disclosure of which is incorporated by reference as if fully set forth herein.

STATEMENT OF GOVERNMENT SUPPORT

This invention was made with government support under GM053386 awarded by the National Institutes of Health. The government has certain rights in the invention.

BACKGROUND OF THE INVENTION

Combined antiretroviral therapy (cART) has had a major impact on the AIDS epidemic; however, no eradication of human immunodeficiency virus type 1 (HIV 1) appears to be readily possible, in part due to the viral reservoirs remaining in blood and infected tissues. Moreover, a number of challenges have been encountered in bringing about the optimal benefits of the currently available therapeutics of HIV 1 infection and AIDS to individuals receiving cART. They include: (i) drug-related toxicities; (ii) partial restoration of immunologic functions once individuals developed AIDS; (iii) development of various cancers as a consequence of survival prolongation; (iv) flaring-up of inflammation in individuals receiving cART or immune reconstitution syndrome (IRS); and (v) increased cost of antiviral therapy. Such limitations and flaws of cART are exacerbated by the development of drug-resistant HIV 1 variants.

One of the sanctuary sites for HIV-1 infection is the central nervous system (CNS). The fact that HIV-1 enters and infects target cells in the CNS represents a significant challenge for the long-term suppression of the virus replication and has been linked to the development of several neurological complications. Although cART has significantly reduced the incidence of HIV-1-associated dementia, the prevalence of CNS disorders such as HIV 1-associated neurocognitive disorders or HAND appears to be increasing as a result of prolonged patient survival and poor antiretroviral drug penetration into the CNS. Furthermore, subtherapeutic drug concentrations in the CNS may facilitate the development of viral resistance. In addition, HIV 1 infection of the CNS may also result in the establishment of a unique viral reservoir, to which certain antiretroviral drugs do not have reasonable access. Moreover, there is evidence that cART is less effective in lowering virus replication in the CNS than in the blood; and, unfortunately, HIV protease inhibitors and several of the nucleoside analogs penetrate only poorly into the CNS, allowing early CNS infection to evolve independently over time in the inaccessible brain reservoir.

Successful antiviral drugs, in theory, exert their virus-specific effects by interacting with viral receptors, virally-encoded enzymes, viral structural components, viral genes, or their transcripts without disturbing cellular metabolism or function. However, at present, no antiretroviral drugs or agents are likely to be completely specific for HIV 1 or to be devoid of toxicity in the therapy of AIDS, which is a critical issue because patients with AIDS and its related diseases will have to receive cART for a long period of time, perhaps for the rest of their lives. Thus, the identification of new class of antiretroviral drugs, which have a unique mechanism(s) of action and produce no or minimal side effects, remains an important therapeutic objective.

One such new class of antiretroviral drugs is non-peptidyl protease inhibitors (PIs) that are potent against HIV-1 variants resistant to the currently approved PIs. One such anti-HIV 1 agent is darunavir (DRV),

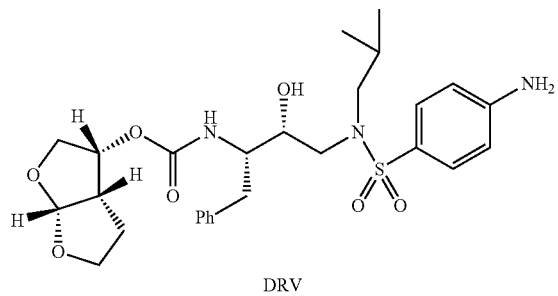 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1 ; "DRV"]

DRV containing a structure-based designed privileged nonpeptidic P2 ligand, 3(R),3a(S),6a(R)-bis-tetrahydrofuranylurethane (bis-THF), has been clinically used worldwide as a first-line therapeutic for HIV-1-infected individuals.

It has been discovered that certain non-peptidic HIV-1 protease inhibitors containing certain gem-difluoro heterobicyclic P2-ligands, such as gem-difluoro bis-THF or tetrahydropyranotetrahydrofuran (THP-THF) derivatives, exert highly potent activity against a wide spectrum of laboratory HIV-1 strains and primary clinical isolates including multi-PI-resistant variants with minimal cytotoxicity.

As described herein for the species denoted as GRL-04810 and GRL-05010,

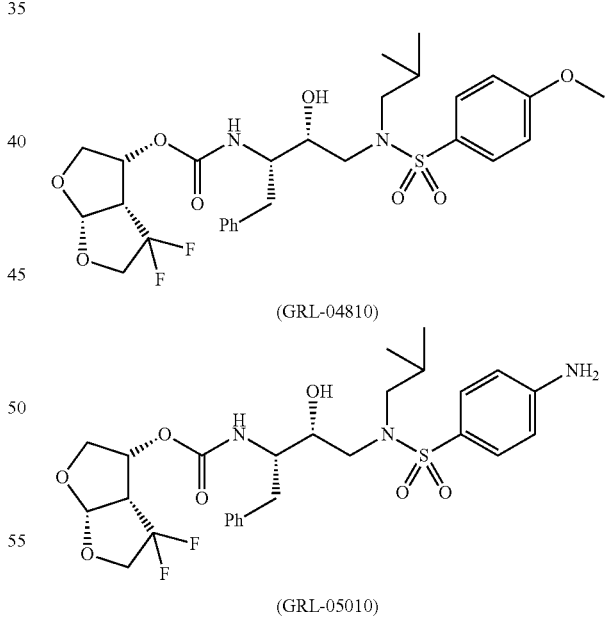

(GRL-04810)

(GRL-05010)

these compounds exert highly potent activity against a wide spectrum of laboratory HIV-1 strains and primary clinical isolates including multi-PI-resistant variants with minimal cytotoxicity. Also described herein is molecular modeling related to the elucidation of the binding interactions of the two compounds with the wild-type HIV-1 protease. In addition, HIV-1 variants were selected with GRL-04810 and GRL-05010, by propagating a laboratory wild-type HIV-1$_{NL4-3}$, in MT-4 cells in the presence of increasing concentrations of GRL-04810 and GRL-05010; and amino acid substitutions that emerged under the pressure of these compounds in the protease-encoding region were determined. Finally, in view of the limited penetration of most antiviral drugs into the CNS, the partition and distribution coefficients (logP and logD), as well as the apparent blood brain barrier (BBB) permeability coefficient (Papp), were evaluated using an in vitro model, where it was demonstrated that GRL-04810 and GRL-05010 had a potentially enhanced penetration capability across the BBB.

MT-4 cells were exposed to the wild type strain HIV-1$_{NL4-3}$ and cultured in the presence of increasing concentrations of GRL-04810 (○), GRL-05010 (●), darunavir (▲) and lopinavir (Δ). Culture supernatants were collected weekly; and, if the amounts of p24 Gag were found to surpass the cutoff value of 200 ng/ml, those supernatants were used for the subsequent passage. Each passage was conducted in a cell-free manner.

Figures 3, 4:
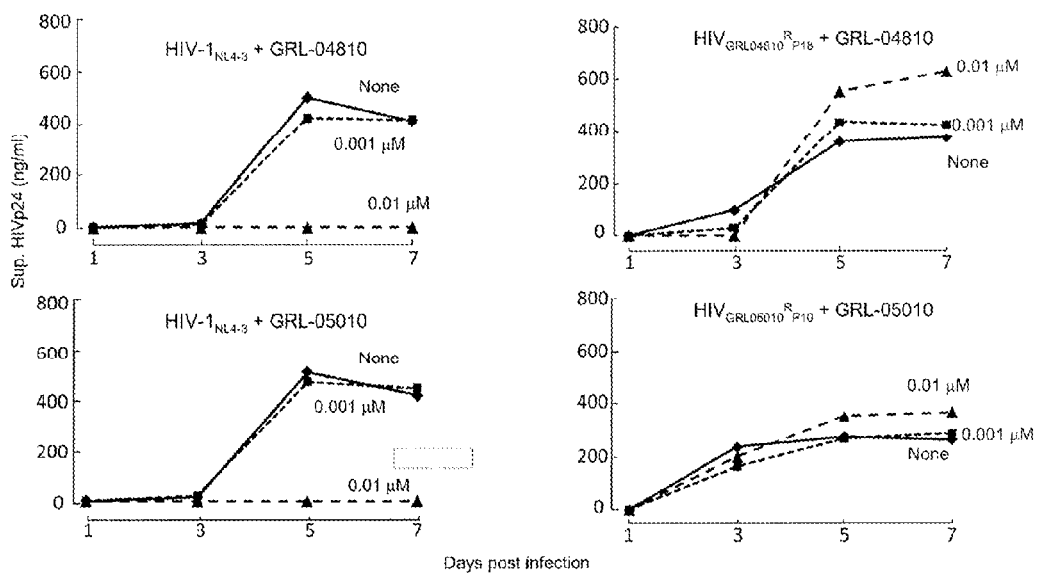

FIG. 3. Amino acid sequences of the protease-encoding region of HIV-1 variants selected in the presence of GRL-04810 and GRL-05010. (SEQ ID NOs:1-12)

Shown are the amino acid sequences deduced from the nucleotide sequences of the protease-encoding region of proviral DNA isolated from HIV-1$_{NL4-3}$ variants selected in the presence of GRL-04810, GRL-05010, and DRV at passages 20, 15, and 20, respectively. Identified amino acid substitutions in the protease-encoding region and their frequencies (the very right column) are shown. The amino acid sequence of the wild type HIV-1$_{NL4-3}$ protease (pNL4-3 PR) is shown at the top as a reference.

FIG. 4. Replication kinetics of GRL-04810 and GRL-05010-resistant HIV-1 variants generated in vitro.

Figure 1:
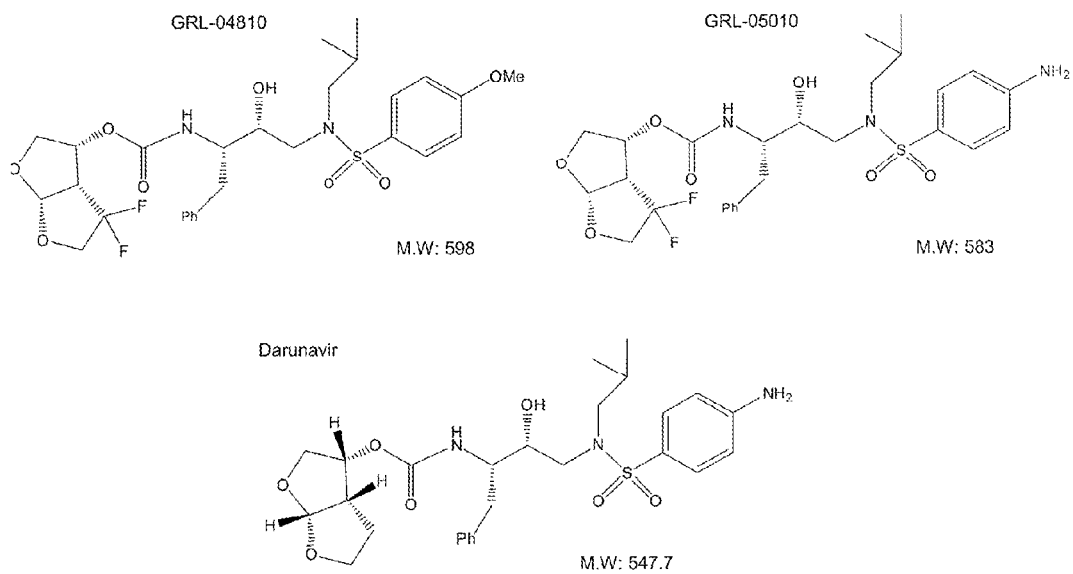
FIG. 1. Structures of GRL-04810, GRL-05010 and darunavir.
Figure 2:
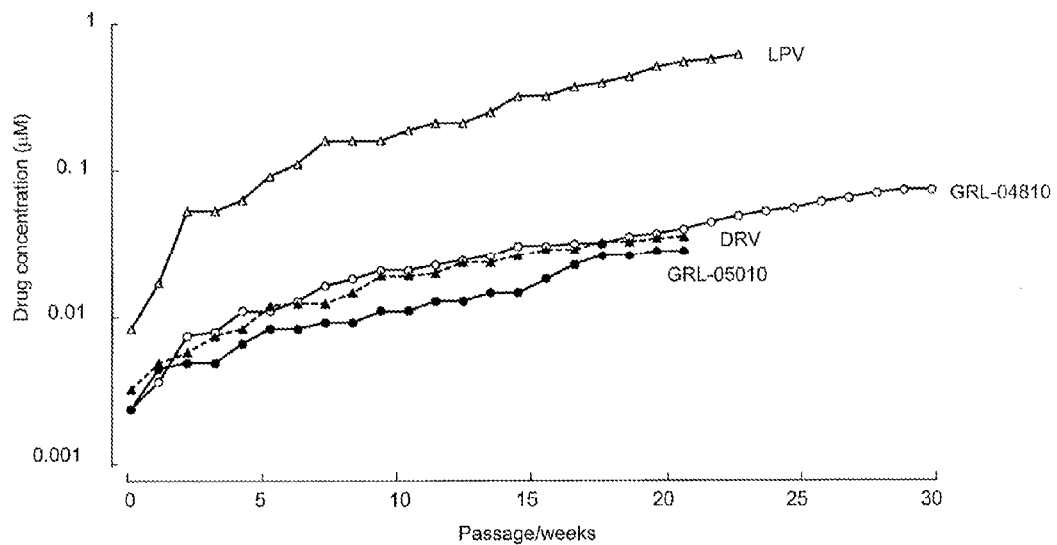
FIG. 2. Selection of in vitro variants resistant to GRL-04810 and GRL-05010.

GRL-04810- and GRL-05010-resistant viruses were obtained from the selection assay illustrated in FIG. 2. Two time point passages, HIV-1$_{GRL-04810}^{R}{}_{P18}$ and HIV-1$_{GRL-05010}^{R}{}_{P10}$, were chosen. HIV-1$_{NL4-3}$ or two resistant viruses were propagated in CD4$^+$ MT-4 cells in the presence of 0.01 µM (▲), 0.001 µM (■) of GRL-04810 and GRL-05010 or in the absence (♦) of the compounds in culture flasks. The amounts of p24 in each culture flask were quantified every two days for one week.

Figure 5A:
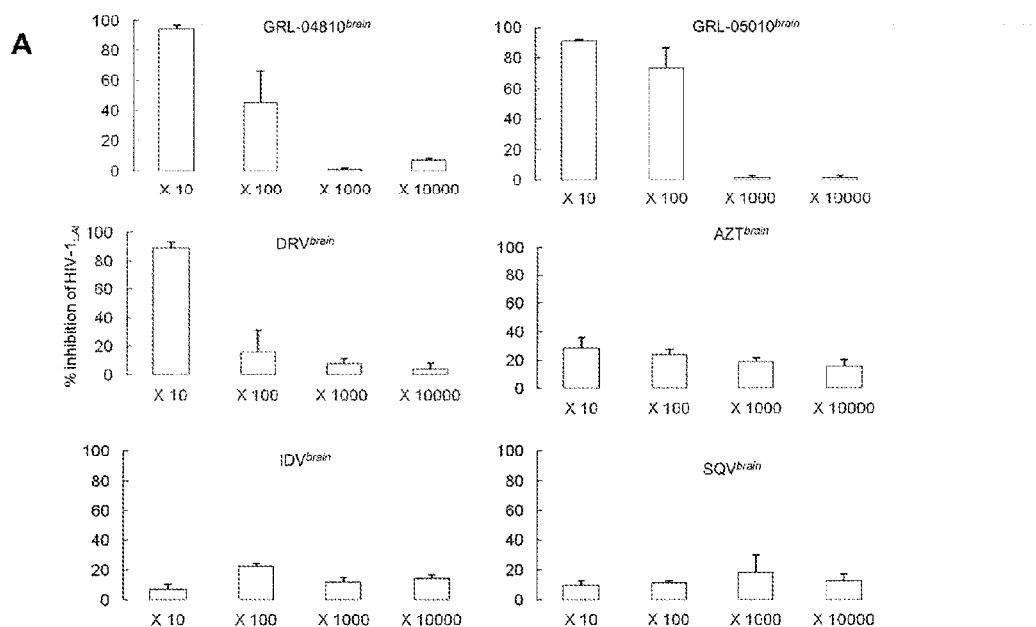
Figure 5B:
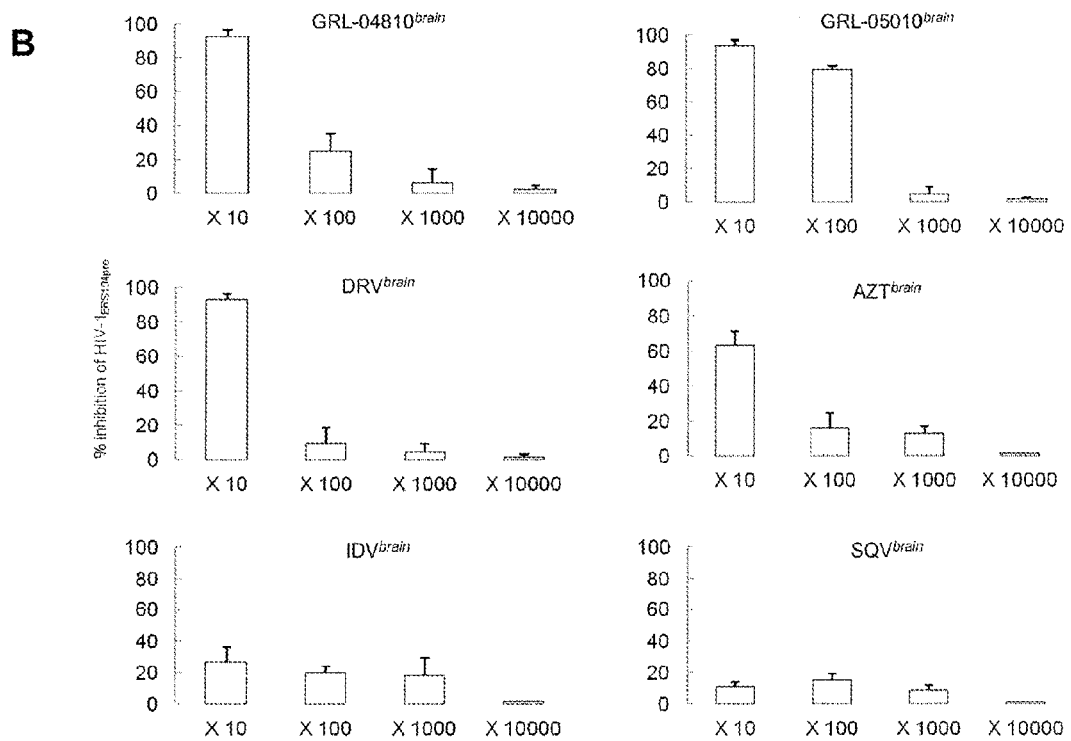

FIGS. 5A and 5B. Antiviral activity of GRL-04810$^{brain}$, GRL-05010$^{brain}$, DRV$^{brain}$, AZT$^{brain}$ (azidothymidine), IDV$^{brain}$ (adefovir dipivoxil) and SQV$^{brain}$ (saquinavir) against HIV-1$_{LAI}$ and HIV-1$_{ERS104pre}$.

The "brain-side" of the medium containing a compound collected in the BBB in vitro assay, was subjected to antiviral assays. Two HIV-1 isolates were employed, HIV-1$_{LAI}$ (Panel A) and HIV-1$_{ERS104pre}$ (Panel B). The "brain-side" media, termed GRL-04810$^{brain}$, GRL-05010$^{brain}$, DRV$^{brain}$, AZT$^{brain}$, IDV$^{brain}$ and SQV$^{brain}$, were challenged with either of the two HIV-1 isolates in MTT assay (Panel A) and p24 assay (Panel B). Dilution ranges were between 10-fold and 10,000-fold, and the percentage of viral inhibition was used as an endpoint. It is deemed that the greater the percentage of inhibition of HIV-1$_{LAI}$ and HIV-1$_{ERS104pre}$, the greater the concentration of the drug in the "brain side" medium. Assays were conducted in duplicate and error bars show standard deviations.

Figure 6:
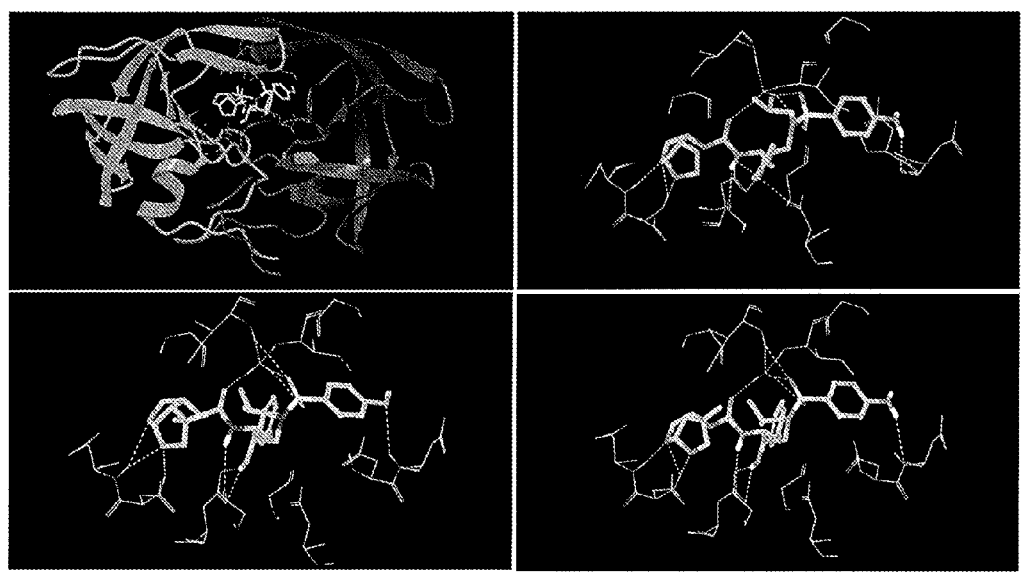

FIG. 6. Structural interactions of GRL-04810 and GRL-05010 with HIV-1 protease.

A model of GRL-04810 bound to protease is shown (Panel A). GRL-04810 is shown in thick sticks and residues in the protease active site are shown in wire. The following atom colors are used: carbons in grey, oxygens in red, fluorines in green, nitrogens in blue, and sulfurs in yellow. The polar interactions (yellow dotted lines) of DRV, GRL-04810, and GRL-05010, along with other residues in the active site, are shown in panels B, C, and D, respectively. Non-polar hydrogens are not shown. Figures were generated using Maestro™ (version 9.3, Schrödinger, LLC, New York, N.Y., 2012).

DETAILED DESCRIPTION OF THE INVENTION

The compounds of the various embodiments of the present invention provide, among other things, therapeutic agents having enhanced penetration capability across the BBB, such that they can enter the CNS to treat an HIV-1 infection in the CNS.

In each of the descriptions and structural formulae herein, it is to be understood that, unless specified to the contrary, all tautomers are included. Thus, for example, a "pyridone-type" structure may be represented by a "hydroxy-pyridine," as well. As used herein, alkyl, alkoxy, etc. denote both straight and branched groups; but reference to an individual radical such as "propyl" embraces only the straight chain ("normal") radical, a branched chain isomer such as "isopropyl" being specifically denoted.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$) or from 1 to 4 carbon atoms ($C_1$-$C_4$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, and isopentyl groups. As used herein, "(1-6C)" has the same meaning as $C_1$-$C_6$.

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups containing one or more oxygen, nitrogen or sulfur atoms, particularly 5- or 6-membered monocyclic or 9- or 10-membered bicyclic groups, each of which may be optionally substituted. Illustrative aromatic heterocyclic groups include mono- or bicyclic, but are not limited to, pyridinyl, pyrimidinyl, pyrazinyl, triazinyl, tetrazinyl, quinolinyl, quinazolinyl, quinoxalinyl, furanyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

The term "optionally substituted" as used herein includes the replacement of hydrogen atoms with other functional groups on the radical that is optionally substituted. Such other functional groups illustratively include, but are not limited to, amino (e.g., $NH_2$, mono-, and di-alkylamino), hydroxyl, halo (e.g., F, Cl, Br, and I), thiol, alkyl, alkoxy, haloalkyl, heteroalkyl, heterocyclyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, heterocyclyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, alkoxy, haloalkyl, heteroalkyl, heterocyclyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, heterocyclyl, aryl, arylalkyl, arylheteroalkyl, heteroaryl, heteroarylalkyl, heteroarylheteroalkyl, and/or sulfonic acid is optionally substituted.

The term "heterocyclyl" as used herein refers to substituted or unsubstituted non-aromatic ring compounds containing 3 or more ring members, of which, one or more is a heteroatom such as, but not limited to, N, O, and S. Thus, a heterocyclyl can be a cycloheteroalkyl. In some embodiments, heterocyclyl groups include 5 to about 20 ring members, whereas other such groups have 5 to about 15 ring members, preferably 5 to about 8 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, and the like.

Some embodiments of the present invention relate to a compound of the formula

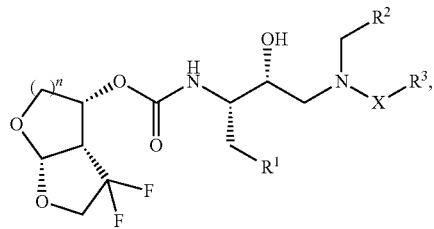

or a pharmaceutically acceptable salt thereof, or a pharmaceutically acceptable salt thereof, wherein:

n is the integer 1 or 2;

$R^1$ is phenyl which is unsubstituted or which bears a fluoro, hydroxymethyl, methoxy or 2-(morpholin-4-yl)ethoxy substituent at the 3- or 4-position, or is 3,5-difluorophenyl;

$R^2$ is 2-propyl or 2-fluoro-2-propyl; and

—X—$R^3$ is selected from the group consisting of —$SO_2$—$R^3$, —C(O)—N(R)—$R^3$, —NH—$SO_2$—$R^3$, and —NH—C(O)—$OR^3$;

in which R is selected from the group consisting of (1-6C) alkyl, aryl, heteroaryl, aryl(1-6C)alkyl or heteroaryl(1-6C) alkyl, each of which is optionally substituted; and $R^3$ is selected from the group consisting of (1-6C)alkyl, aryl, heteroaryl, aryl(1-6C)alkyl or heteroaryl(1-6C)alkyl, each of which is optionally substituted.

In some embodiments, $R^1$ is phenyl, 3-methoxyphenyl or 4-methoxyphenyl. In some examples, $R^1$ is phenyl.

In some embodiments, $R^2$ is 2-propyl.

In some embodiments, —X—$R^3$ is —$SO_2$—$R^3$.

In some embodiments, $R^3$ is selected from the group consisting of 4-aminophenyl, 4-methoxyphenyl, 4-hydroxymethylphenyl, 3-fluoro-4-methoxyphenyl, 4-amino-3-fluorophenyl, 3,4-methylenedioxyphenyl, benzoxazole-6-yl bearing a methyl, methylsulfonyl, dimethylamino or —NH—$R^4$ group at the 2-position; benzothiazole-6-yl bearing a methyl, methylsulfonyl, dimethylamino or —NH—$R^4$ group at the 2-position; and benzimidazole-5-yl bearing a methyl or —NH—$R^4$ group at the 2-position; and $R^4$ is selected from the group consisting of methyl, prop-2-yl, cyclopropyl, isobutyl, tert-butyl, cyclobutyl, cyclopentyl, cyclohexyl, piperidin-4-yl, 1-methylpiperidin-4-yl, 1-(prop-2-yl) piperidin-4-yl and 1-cyclopentylpiperidin-4-yl.

In other embodiments, $R^3$ is selected from the group consisting of 4-aminophenyl, 4-methoxyphenyl, and 3-fluoro-4-methoxyphenyl; $R^3$ is 2-(prop-2-ylamino)benzoxazole-6-yl; or $R^3$ is benzothiazole-6-yl bearing a methylsulfonyl, dimethylamino, 2-(prop-2-ylamino)-, cyclopropylamino, isobutylamino, tert-butylamino, cyclohexylamino, piperidin-4-ylamino, or 1-cyclopentylpiperidin-4-ylamino group at the 2-position.

In some embodiments, R is hydrogen or methyl.

In some embodiments, n is the integer 1 or n is the integer 2.

In still other embodiments, n is the integer 1 or 2; $R^1$ is phenyl, 3-methoxyphenyl or 4-methoxyphenyl; $R^2$ is 2-propyl or 2-fluoro-2-propyl; —X—$R^3$ is —SO$_2$—$R^3$; and $R^3$ is selected from the group consisting of 4-aminophenyl, 4-methoxyphenyl, 3-fluoro-4-methoxyphenyl; 2-(prop-2-ylamino)benzoxazole-6-yl; and benzothiazole-6-yl bearing a methylsulfonyl, dimethylamino, 2-(prop-2-yl-amino)-, cyclopropylamino, isobutylamino, tert-butylamino, cyclohexylamino, piperidin-4-ylamino, or 1-cyclopentylpiperidin-4-ylamino group at the 2-position.

Embodiments of the present invention include compounds selected from the group consisting of:

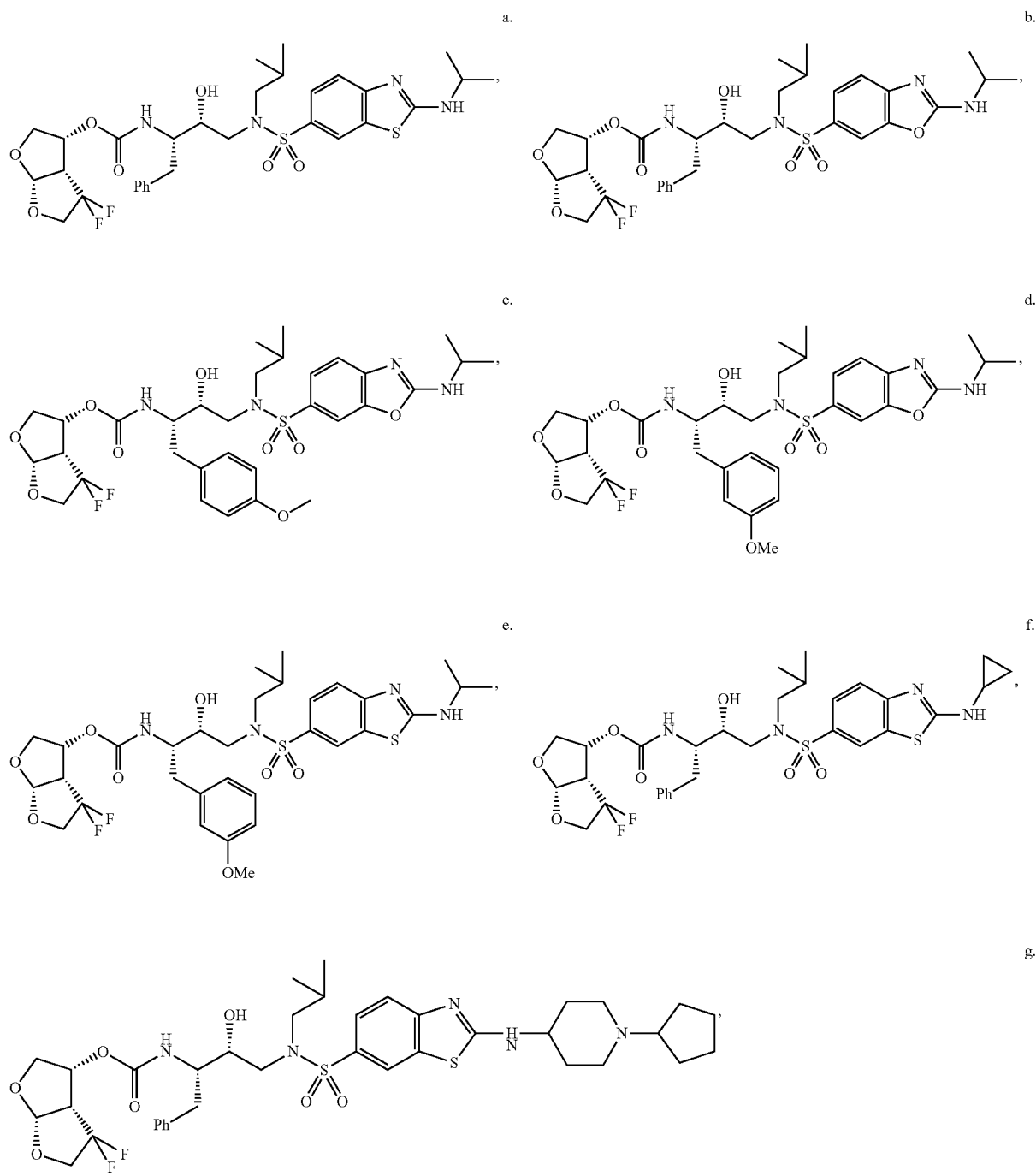

-continued
h.
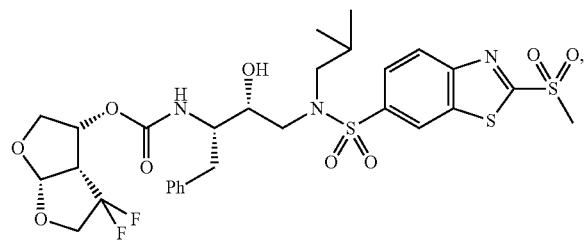
i.
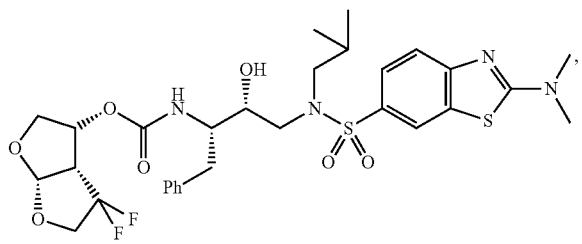
j.
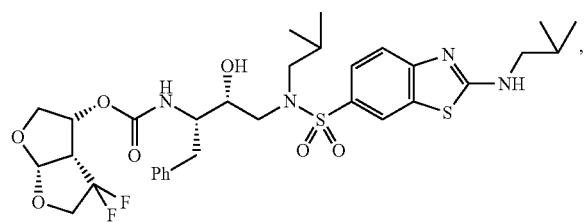
k.
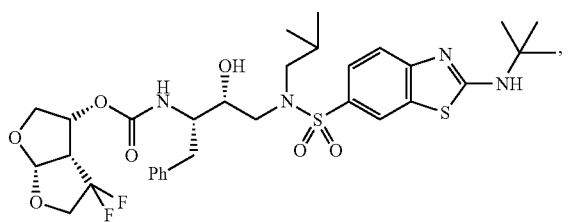
l.
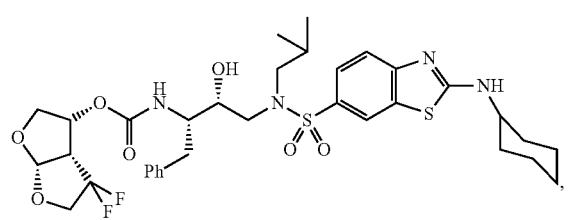
m.
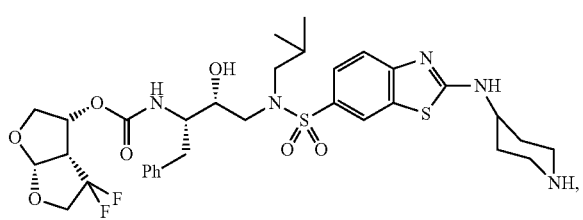
n.
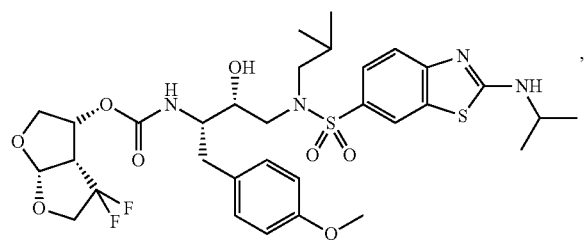
o.
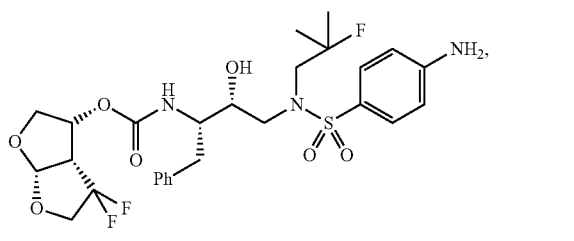
p.
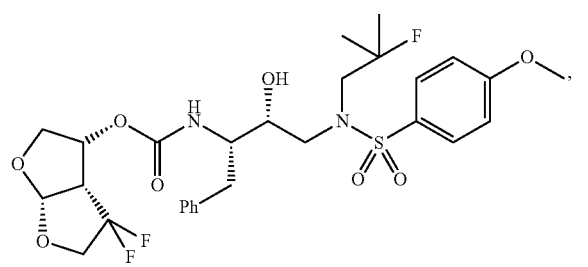
q.
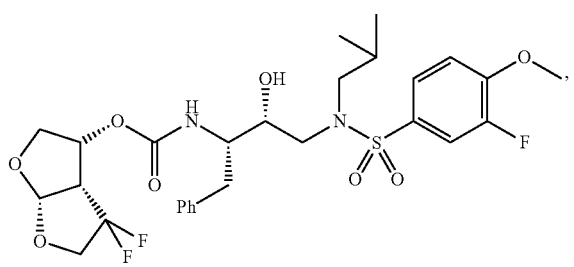
r.
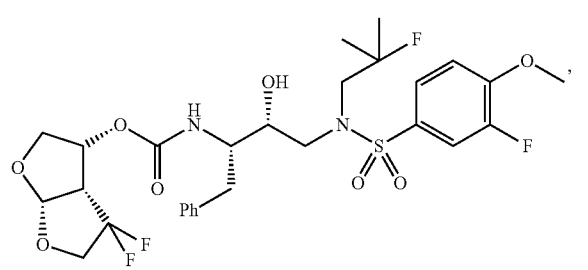
s.
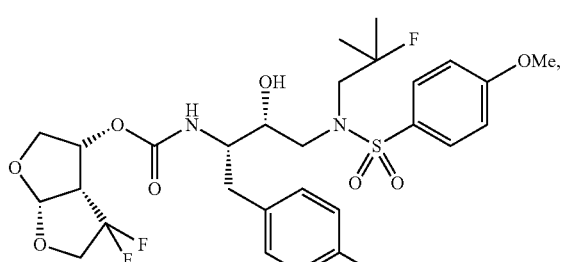

u.
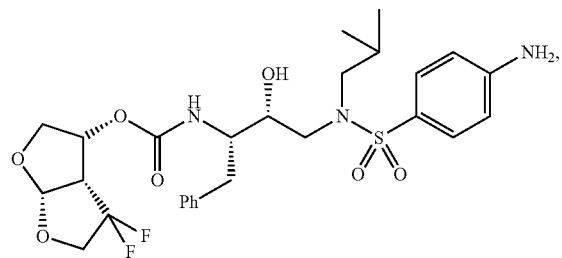
v.
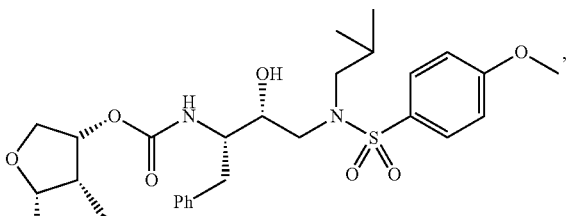
w.
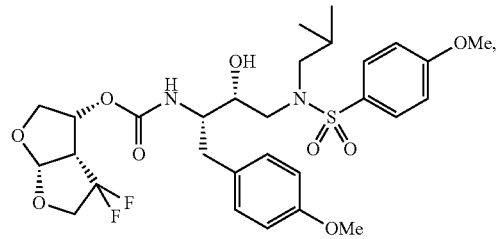
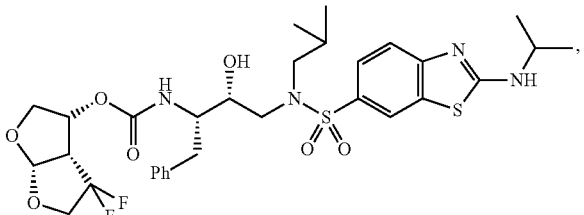
x.
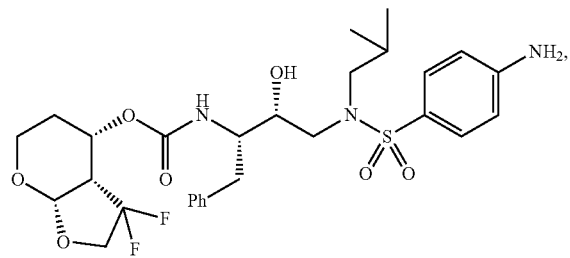
y.
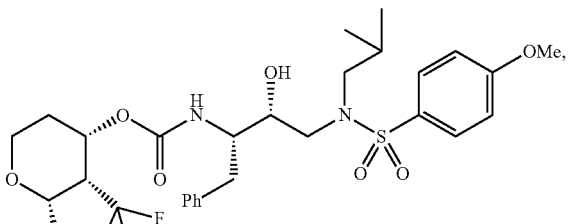
z.
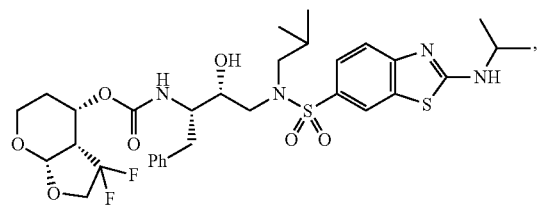
aa.
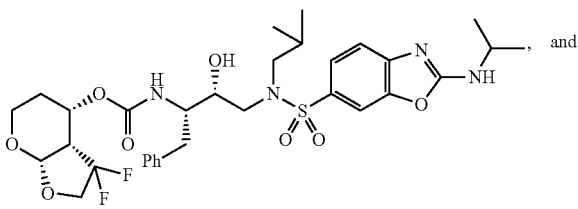
and
ab.
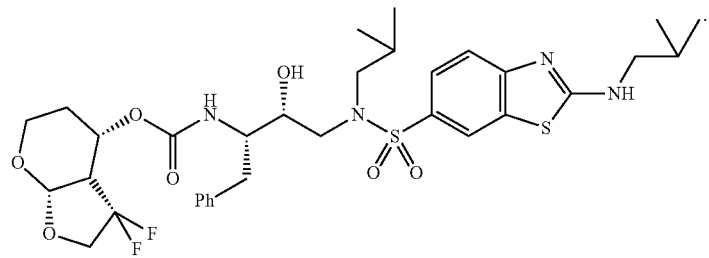
Other embodiments of the present invention include compounds selected from the group consisting of:
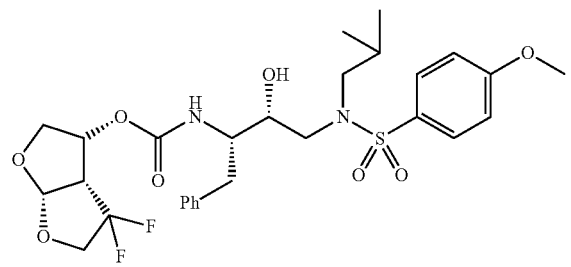
-continued
and
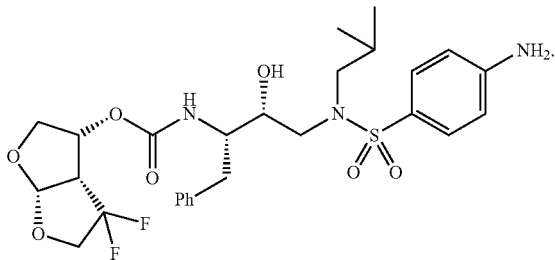

Still other embodiments of the present invention include compounds selected from the group consisting of:

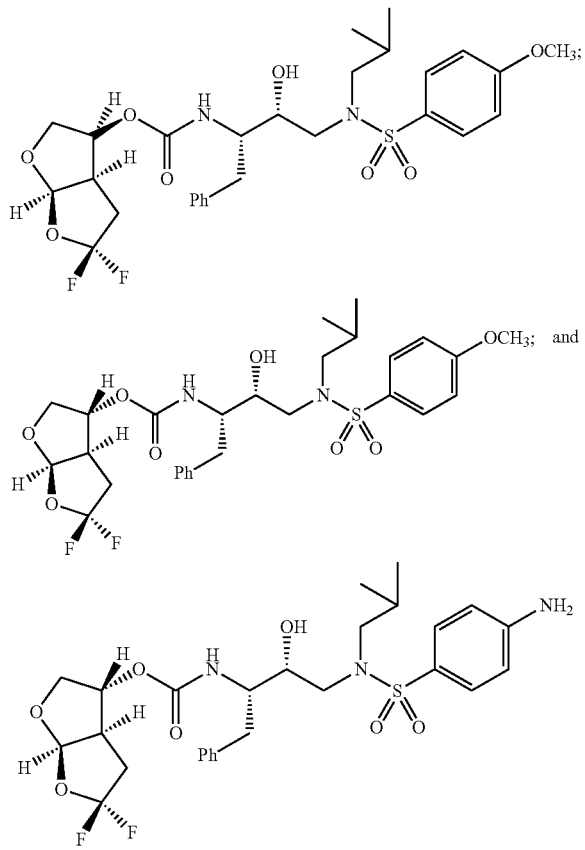

Embodiments of the present invention also relate to synthetic intermediates, including a compound of the formula

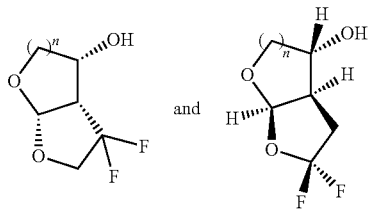

wherein n is the integer 1 or 2. In some embodiments, n is the integer 1. In other embodiments, n is the integer 2.

The compounds of the various embodiments of the present invention can be prepared using the synthetic processes described herein or by one analogous thereto or by a procedure which is selected from standard techniques of organic chemistry, including aromatic substitution and transformation, from techniques which are analogous to the syntheses of known, structurally similar compounds, and techniques which are analogous to the above described procedures or procedures described herein.

If not commercially available, a necessary starting material for the preparation of a compound of the formula described herein may be prepared by a novel process described herein or one analogous thereto or by a procedure which is selected from standard techniques of organic chemistry, including aromatic substitution and transformation, from techniques which are analogous to the syntheses of known, structurally similar compounds, and techniques which are analogous to the above-described procedures or procedures described herein. It will be clear to one skilled in the art that a variety of sequences is available for the preparation of the starting materials. A novel intermediate or starting material compound provides a further aspect of the invention.

DRV is an HIV-1 protease inhibitor, which was most recently added to the armamentarium of antiretroviral therapeutics. DRV exerts highly potent activity against a wide spectrum of multi-drug resistant HIV-1 variants including multi-PI-resistant variants and has been shown to resist to the emergence of DRV-resistant HIV-1 strains in vitro and in the clinical setting. The mechanism(s) of the favorable antiretroviral activity and delayed emergence of DRV-resistant strains include the presence of a unique moiety, bis-THF, in the P2' site and DRV's dual action to block HIV-1 protease's enzymatic activity and protease's dimerization. However, the penetration of DRV into the cerebrospinal fluid (CSF) is only moderate with a ratio of DRV concentration in the CSF over that in peripheral blood being 0.6%, probably due to the only moderate penetration of DRV through the blood-brain-barrier. Herein are described the results with two newly designed, synthesized, and characterized PIs, GRL-04810 and GRL-05010, which contain a bis-THF moiety to which a gem-difluoride group is attached to increase lipophilicity and possibly enhance CSF penetration. See the Examples herein and references cited therein.

In some embodiments, therefore, the invention relates to a method for treating a patient in need of relief from an HIV infection, the method comprising the step of administering to a patient in need of relief from the HIV infection a therapeutically effective amount of one or more compounds of the various embodiments of the present invention.

GRL-04810 and GRL-05010 suppressed various HIV-1 isolates including multi-drug-resistant clinical HIV-1 isolates with reasonably low $EC_{50}$ values and favorable cytotoxicity profiles, although as in the case of DRV, both PIs failed to efficiently block the replication of APV-resistant strains. It seems that the suppression failure of APV-resistant variants has largely been seen in all the bis-THF-containing PIs thus far published. Without being bound by theory, it is thought that the reduced activity of the bis-THF-containing PIs to block the replication of APV-resistant variants is likely due to the structural similarity between the bis-THF-containing PIs including GRL-04810, GRL-05010 and DRV. In the present wild type HIV-$1_{NL4-3}$ selection experiment with the two PIs, the development of resistance against each compound exhibited different patterns compared to two control PIs, LPV and DRV. In the case of GRL-05010, by passage 10, two PI-resistance-associated amino acid substitutions (M46I and I50V) were identified, while HIV-$1_{NL4-3}$ exposed to GRL-04810 acquired three amino acid substitutions: A28S, L33F, and V82I by passage 20 in 5 of 22 clones examined (FIG. 3). The emergence of A28S substitution has previously been documented as a resistance-conferring amino acid substitution when HIV-$1_{NL4-3}$ was selected with two bis-THF containing PIs, TMC-126 (35) and GRL-1398 (32), both of which also contain a para-methoxy group in the P2' site. When HIV-$1_{NL4-3}$ was selected with GRL-0519, which contains the same para-methoxy group in the P2' site, the A28S substitution never appeared by up to passage 37. GRL-0519 has tris-THF as the P2 ligand and the para-methoxy moiety at the P2' site, suggesting that the presence of tris-tetrahydrofuranylurethane (tris-THF) prevented the selection of the A28S substitution. Indeed, it seems that, even with long-term administration of DRV, HIV-1 containing the A28S substitution has not been documented in the clinical settings. Considering that the selection of HIV-1$_{NL4-3}$ and even a mixture of 8 multi-PI-resistant clinical strains with DRV failed to select out the A28S substitution (36) and that only GRL-04810 selection of HIV-1$_{NL4-3}$ resulted in the emergence of the A28S substitution in the present study, the combination of bis-THF as the P2 ligand and the para-methoxy moiety at the P2' site seems to be associated with the emergence of the A28S substitution. As illustrated in FIG. 3, it is of note that the emergence of 2 to 3 amino acid substitutions known to be associated with HIV-1's acquisition of PI resistance in the selection assays with the two novel PIs and no emergence of amino acid substitutions in the selection with DRV may possibly pose a disadvantage of GRL-04810 and GRL-05010 with respect to DRV. Zidovudine (ZDV) is the only ARV agent with demonstrated efficacy in the treatment of HIV-1-associated dementia. Considering that HIV-1 causes CNS diseases ranging from HIV-1-associated neurocognitive disorders (HAND) and the milder but also serious presentation, HIV-1-associated minor cognitive/motor disorder (MCMD), to the devastating HIV-1-associated encephalopathy, more effective ARV regimens with agents exerting maximal penetration of the BBB are urgently needed. It is well established that the lipophilicity of a molecule is one of the crucial determinants of the molecule's druglikeness including the absorption through the digestive tract, penetration of the target cells, oral bioavailability, and penetration through BBB (37, 39). The shake flask method represents a reasonable way to determine the partition and distribution coefficients of molecules to be tested. The partition (logP) coefficient is an estimate of a compound's overall lipophilicity, which is associated with the compound's solubility, permeability through biological membranes, hepatic clearance, lack of selectivity and non-specific toxicity. In the present study, the logP determination of GRL-04810 gave a higher concentration in the octanol (lipidic) interface than GRL-05010 and DRV (Table 4). To estimate the actual figures for the ionized form of the drugs (logD) tris-buffered saline (pH 7.4) must be employed. In both assays the values displayed by both GRL-05010 and DRV were within the acceptable range for the optimal lipophilicity of drug candidates.

Cell-culture-based models have greatly contributed to the understanding of the physiology, pathology and pharmacology of the blood-brain barrier. Indeed, certain in vitro BBB models have proven to serve as useful tools that permit the estimation of the apparent penetration of molecules into the CNS. GRL-04810 and GRL-05010 gave reasonably favorable indexes suggesting potentially favorable penetration ability across the BBB as compared to DRV and other anti-HIV-1 drugs examined in the present study including AZT, IDV, SQV, LPV and ATV.

A well-characterized in vitro BBB cell model can also provide a valuable tool for studying mechanistic aspects of transport as well as biological and pathological processes related to the BBB. To use any in vitro BBB cell model successfully it needs to fulfill a number of criteria, such as reproducible permeability of reference compounds, good screening capacity, the display of complex tight junctions, adequate expression of BBB phenotypic transporters and transcytotic activity. The BBB model employed in the present study complies with all of these parameters and provides an additional advantage as it incorporates a trilayer of cells consisting of astrocytes, pericytes and brain endothelial cells, thus increasing its anatomical and physiological reliability. Molecules and compounds that reach Papp values greater than $20 \times 10^{-6}$ cm/s are deemed to be favorable in terms of relative penetration across the BBB. Conversely those that display values between 2 and $10 \times 10^{-6}$ cm/s are defined as compounds with low BBB penetration. In the present work, both GRL-05010 and GRL-04810 showed the highest values of Papp with $47.8 \times 10^{-6}$ and $61.8 \times 10^{-6}$ cm/s, respectively, among the protease inhibitors examined (Table 5).

As to whether GRL-04810 and GRL-05010 harvested from the "brain interface" in the BBB model retained antiviral activity, both GRL-04810 and GRL-05010 recovered (termed GRL-04810$^{brain}$ and GRL-05010$^{brain}$) significantly more profoundly suppressed the replication of HIV-1$_{LAI}$ and HIV-1$_{ERS104pre}$ than other antiretroviral agents including DRV (FIG. 5), strongly suggesting that both GRL-04810 and GRL-05010 that crossed into the brain interface in the BBB assay were molecularly intact and exerted robust anti-HIV-1 activity.

The present data suggest that GRL-04810 and GRL-05010 have several advantages: (i) they exert potent activity against a wide spectrum of drug-resistant HIV-1 variants, presumably due to its interactions with the main chains of the active site amino acids Asp29 and Asp30; (ii) they have a good lipophilicity profile as expressed by the logD values; and (iii) they have apparently favorable penetration across the BBB.

In another embodiment, pharmaceutical compositions containing one or more of the compounds are also described herein. In one aspect, the compositions include a therapeutically effective amount of the one or more compounds for treating a host animal with HIV-1. It is to be understood that the compositions may include other components and/or ingredients, including, but not limited to, other therapeutically active compounds, and/or one or more carriers, diluents, excipients, and the like, and combinations thereof. In another embodiment, methods for using the compounds and pharmaceutical compositions for treating host animals with HIV-1 are also described herein. In one aspect, the methods include the step of administering one or more of the compounds and/or compositions described herein to a host animal with HIV-1. In another aspect, the methods include administering a therapeutically effective amount of the one or more compounds and/or compositions described herein for treating host animals with HIV-1. In another embodiment, uses of the compounds and compositions in the manufacture of a medicament for treating host animals with HIV-1 are also described herein. In one aspect, the medicaments include a therapeutically effective amount of the one or more compounds and/or compositions for treating a host animal with HIV-1.

It is to be understood herein that the compounds described herein may be used alone or in combination with other compounds useful for treating HIV-1, including those compounds that may be therapeutically effective by the same or different modes of action. In addition, it is to be understood herein that the compounds described herein may be used in combination with other compounds that are administered to treat other symptoms of HIV-1, such as compounds administered to treat infections, and the like.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures. See generally, Remington: The Science and Practice of Pharmacy, ($21^{st}$ ed., 2005).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a co-therapy.

In addition to the illustrative dosages and dosing protocols described herein, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "administering" as used herein includes all means of introducing the compounds and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and/or vehicles.

Illustrative formats for oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

Illustratively, administering includes local use, such as when administered locally to the site of disease, injury, or defect, or to a particular organ or tissue system. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the host animal being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

Depending upon the disease as described herein, the route of administration and/or whether the compounds and/or compositions are administered locally or systemically, a wide range of permissible dosages are contemplated herein, including doses falling in the range from about 1 μg/kg to about 1 g/kg. The dosages may be single or divided, and may administered according to a wide variety of protocols, including q.d., b.i.d., t.i.d., or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

When given systemically, such as parenterally, illustrative doses include those in the range from about 0.01 mg/kg to about 100 mg/kg, or about 0.01 mg/kg to about 10 mg/kg, or about 0.1 mg/kg to about 100 mg/kg, or about 0.1 mg/kg to about 10 mg/kg.

When given systemically, such as orally, illustrative doses include those in the range from about 0.1 mg/kg to about 1000 mg/kg, or about 0.1 mg/kg to about 100 mg/kg, or about 0.1 mg/kg to about 10 mg/kg, or about 1 mg/kg to about 1000 mg/kg, or about 1 mg/kg to about 100 mg/kg, or about 1 mg/kg to about 10 mg/kg.

In another illustrative embodiment, such as when treating a systemic condition, the compound is administered parenterally systemically q.d. at a dose of about 0.1 mg/kg, or about 0.5 mg/kg, or about 1 mg/kg, or about 5 mg/kg, or about 10 mg/kg, or about 50 mg/kg of body weight of the host animal.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Illustrative examples of suitable excipients include lactose, dextrose, sucrose, sorbitol, mannitol, starches, gum *acacia*, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the host animal by employing procedures known in the art. It is to be understood that one or more carriers, one or more diluents, one or more excipients, and combinations of the foregoing may be used in making the pharmaceutical compositions described herein. It is appreciated that the carriers, diluents, and excipients used to prepare the compositions described herein are advantageously GRAS (generally regarded as safe) compounds.

Illustrative examples of emulsifying agents include naturally occurring gums (e.g., gum *acacia* or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

Controlled Release Oral Dosage Forms. Controlled release compositions for oral use may, e.g., be constructed to release the active drug by controlling the dissolution and/or the diffusion of the active drug substance.

Liquids for Oral Administration. Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

Parenteral Compositions. The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions described herein may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions. Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of micro spheres and/or microcapsules are, e.g., biodegradable/bioerodible polymers such as polygalactin, poly-(isobutyl cyanoacrylate), poly(2-hydroxyethyl-L-glutamnine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)).

Intraocular and/or Periocular Compositions: The pharmaceutical composition can also be included in any suitable pharmaceutical preparation or system for administration via intraocular or periocular routes of administration, together with pharmaceutically acceptable carriers, adjuvants or vehicles. Targeting of ocular tissues may be accomplished in any one of a variety of ways. The pharmaceutical preparation for intraocular or periocular administration may also include one or more excipient components, such as effective amounts of buffering agents, preservatives, emulsifiers, salts, lubricants, polymers, solvents, and other known excipients for ocular pharmaceutical formulations, and the like. In one embodiment, the pharmaceutical composition includes an emulsifier and a buffered carrier such as Polysorbate 80 in HBSS (Hank's Balanced Salt Solution).

The pharmaceutical preparation can be administered by any route of ocular administration known in the art including, but not limited to, topical ocular, subtenons, subconjunctival, intracameral, or intravitreal routes. In one embodiment, the pharmaceutical preparation can be delivered topically, e.g., via an eye drop, gel, ointment, or salve. In other embodiments, the pharmaceutical preparation can be delivered via an acute delivery system, e.g., using nanotubes, local injection, micro-injection, syringe or scleral deposition, or ultrasound.

Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9, and more preferably about 4 to about 8. As such the buffering agent may be as much as about 5% by weight of the total system.

Suitable water soluble preservatives include sodium bisulfite, sodium bisulfate, sodium thio sulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. Such agents may be present in amounts as needed, such as from about 0.001 to about 5% by weight, or from about 0.01 to about 2% by weight.

Intraocular Compositions for injection are described herein and include injection into the aqueous or vitreous humor of the eye. In one embodiment, the compounds and/or compositions described herein are administered via intraocular sustained delivery (such using VITRASERT or ENVISION, or related technologies). In another embodiment, the compounds and/or compositions are delivered by posterior suborbital injection.

Compositions for Inhalation. For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

Percutaneous and Topical Compositions. The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

Rectal Compositions. For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols and polvoxyethylene sorbitan fatty acid esters. Various additives, enhancers, or surfactants may be incorporated.

The effective use of the compounds, compositions, and methods described herein for treating or ameliorating one or more effects of an HIV-1 associated disease using one or more compounds described herein may be based upon animal models, such as murine, canine, porcine, and non-human primate animal models of disease. For example, it is understood that HIV-1 associated disease in humans may be characterized by a loss of function, and/or the development of symptoms, each of which may be elicited in animals, such as mice, and other surrogate test animals.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

The following examples further illustrate specific embodiments of the invention; however, the following illustrative examples should not be interpreted in any way to limit the invention.

Synthesis and Compound Examples

Examples of general preparations of the inhibitors of the invention are described as follows:

Synthesis of 4,4-difluoro-bis-THF (n=1)

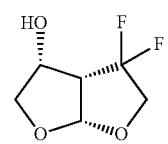

1

Synthesis of α,β-Unsaturated Ester 4:

Methyl ester 2 (3.01 g, 10.0 mmol) was dissolved in dichloromethane (50.0 mL) and cooled to −78° C. To the solution was added DIBAL (1.0 M in DCM, 15.0 mL, 15.0 mmol), and the mixture was stirred for 1.5 hour. The reaction was quenched by sat. aq. Rochelle salt, and the whole mixture was stirred overnight until the aqueous phase became clear. The organic phase was then washed with brine, dried over sodium sulfate, filtered, and evaporated in vacuo to give crude aldehyde 3 (2.85 g), which was immediately subjected to the next HWE reaction. A suspension of sodium hydride (60% dispersion in mineral oil, 1.48 g, 37.0 mmol) in tetrahydrofuran (30 mL) was cooled down to 0° C., and to the suspension was dropwise added triethyl phosphonoacetate (7.95 mL, 40.1 mmol). After 30 mins, the reaction mixture was neutralized with sat. aq. ammonium chloride and extracted with ethyl acetate. The organic layer was washed with brine, dried over sodium sulfate, filtered, and evaporated in vacuo. The residue was purified through silica gel column chromatography (Hexanes/AcOE=20/1) to give unsaturated ethyl ester 4 (2.99 g, 8.78 mmol, 88% for two steps) as colorless oil. $^1$H-NMR spectrum was consistent with the spectrum reported in the reference[1]. Optical rotation had the opposite sign with the almost same value: $[\alpha]_D^{20}$=−23.4 (c 1.39, CHCl$_3$) (lit. $[\alpha]_D^{20}$=+19.2 (c 1.45, CHCl$_3$)).

2

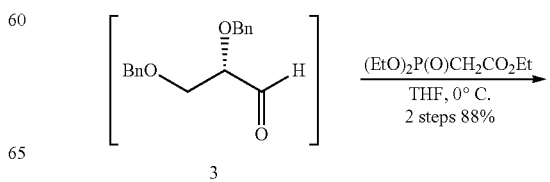

3

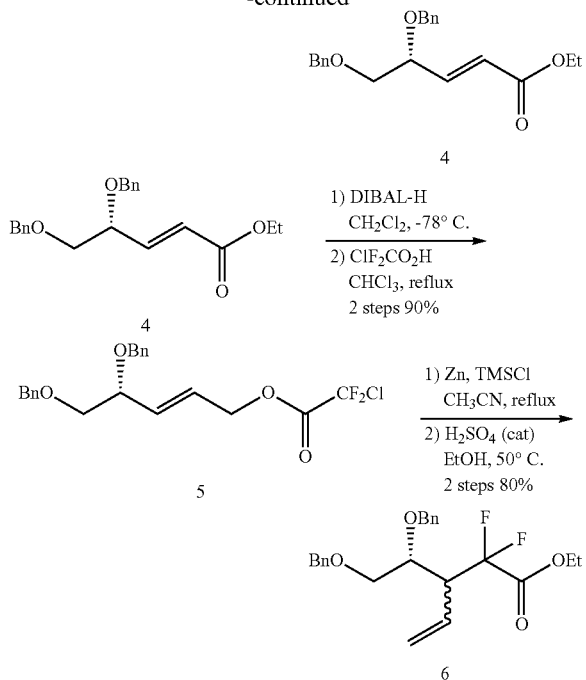

Synthesis of Fluroester 5:

Difluorochloroacetate 5 was obtained according to the known scheme, which is reported in *Org Lett*. 2007, 9, 5437. Difluorochloroacetate 5 was synthesized in 90% yield following the procedure reported in the reference. $^1$H-NMR spectrum was consistent with the spectrum reported in the reference[1]. Optical rotation had the opposite sign with the almost same value: $[\alpha]_D^{20}=-15.4$ (c 1.08, CHCl$_3$) (lit. $[\alpha]_D^{20}=+13.4$ (c 1.75, CHCl$_3$)).

The dia-stereoselectivity of the Reformatskii-type rearrangement reaction was 2/1 (the reference reported that it was 3/1). The diasteromixture 6 was separated by column chromatography after converting them to the corresponding Weinreb amides 7 and 8. The amides were reduced by DIBAL and NaBH$_4$ in one pot to provide alcohols 9 and 10 respectively.

Synthesis of Weinreb Amides 7 and 8:

Weinreb amides 7 and 8 were synthesized in 66% and 33% yields respectively from ethyl ester 6, which was made from difluoroacetate 5 in 80% following the procedure reported in *Org Lett*. 2007, 9, 5437. $^1$H-NMR spectra were consistent with the spectra reported in the reference. Optical rotation had the opposite sign with the almost same value: for 7, $[\alpha]_D^{20}=-25.1$ (c 1.07, CHCl$_3$) (lit. $[\alpha]_D^{20}=+28.0$ (c 0.75, CHCl$_3$)), for 8, $[\alpha]_D^{20}=-18.0$ (c 0.55, CHCl$_3$) (lit. $[\alpha]_D^{20}=+19.6$ (c 0.60, CHCl$_3$)).

Synthesis of Alcohol 9:

Weinreb amide 7 (270 mg, 644 μmol) was dissolved in tetrahydrofuran (10 mL). To the solution was added LAH (77.0 mg, 2.03 mmol) at 0° C., and the reaction mixture was stirred for 30 mins. The reaction was quenched by adding water and 3 M aq. NaOH. After the resultant mixture was diluted with diethyl ether, small amount of NaBH$_4$ was added to it. The reaction mixture was stirred overnight, filtered, and purified through silica gel column chromatography (1% methanol in DCM) to give alcohol 9 (231 mg, 637 μmol, 99%) as clear oil. $^1$H-NMR (400 MHz, CDCl$_3$): δ 7.40-7.31 (m, 10H), 5.92 (dt, J=17.2, 10.0 Hz, 1H), 5.35-5.23 (m, 2H), 4.79-4.49 (m, 4H), 4.15-4.11 (m, 1H), 3.83-3.49 (m, 4H), 3.05-3.00 (m, 1H), 2.70 (br, 1H). $^{13}$C-NMR (100 MHz, CDCl$_3$): δ 137.83, 129.95, 128.38, 127.86, 127.80, 127.73, 127.68, 122.62 (t, J=245.7 Hz), 122.03, 75.72, 73.31, 73.04, 70.23, 63.27 (t, J=30.6 Hz), 50.20 (t, J=22.7 Hz). $^{19}$F-NMR (376 MHz): δ−109.61 (ddd, J=251.9, 26.3, 15.1 Hz), −111.29 (ddd, J=251.9, 30.1, 15.1 Hz). $[\alpha]_D^{20}=-17.9$ (c 0.66, CHCl$_3$). LRMS (CI): 361 (M−H)$^+$.

Synthesis of Alcohol 10:

Alcohol 10 was obtained in 96% from Weinreb amide 8 through the same procedure as when alcohol 9 was obtained. $^1$H-NMR (400 MHz, CDCl$_3$): δ 7.40-7.32 (m, 10H), 5.78 (dt, J=17.4, 9.8 Hz, 1H), 5.36-5.29 (m, 2H), 4.83 (d, J=11.1 Hz, 1H), 4.60-4.52 (m, 3H), 3.96-3.61 (m, 5H), 3.23-3.10 (m, 1H), 3.00 (br, 1H). $^{13}$C-NMR (100 MHz, CDCl$_3$): δ 137.95, 137.41, 130.37, 128.51, 128.38, 128.06, 128.00, 127.69, 122.77 (t, J=245.3 Hz), 121.46, 77.20, 73.38, 72.80, 70.49, 63.87 (dd, J=33.8, 30.2 Hz), 49.99 (t, J=23.0 Hz). $^{19}$F-NMR (376 MHz): δ−104.01 (multiplet), −113.05 (multiplet). $[\alpha]_D^{20}=+9.9$ (c 1.06, CHCl$_3$). LRMS (CI): 363 (M+H)$^+$.

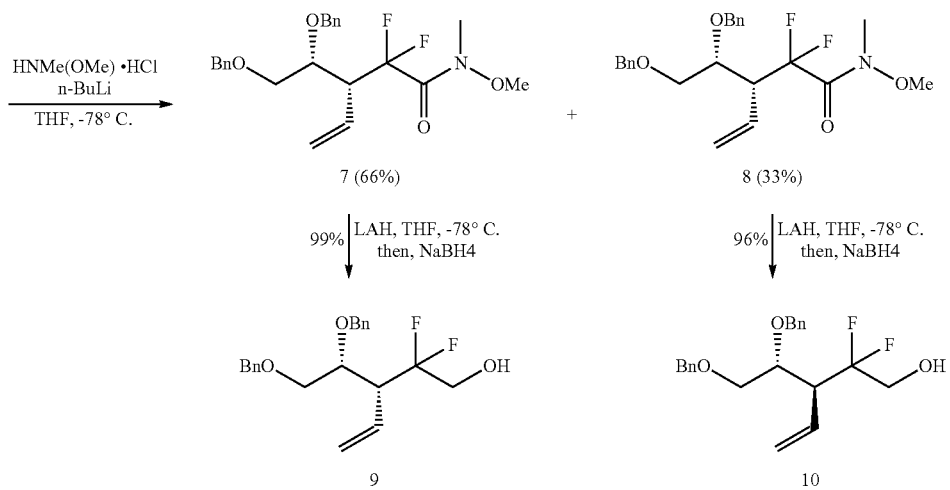 [SMILES: C=C[C@H]([C@H](COCc1ccccc1)OCc1ccccc1)C(F)(F)C(=O)N(C)OC ; C=C[C@H]([C@H](COCc1ccccc1)OCc1ccccc1)C(F)(F)C(=O)N(C)OC ; C=C[C@H]([C@H](COCc1ccccc1)OCc1ccccc1)C(F)(F)CO ; C=C[C@@H]([C@H](COCc1ccccc1)OCc1ccccc1)C(F)(F)CO]

Alcohol 9 was converted to bis-THF alcohol 1 as follows:

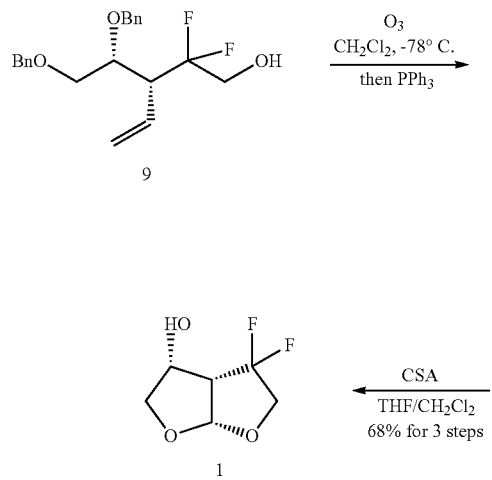

Synthesis of 4,4-difluoro-bis-THF (1):

Alcohol 9 (352 mg, 971 μmol) was dissolved in dichloromehane (30.0 mL), and ozone was bubbled into the solution for 5 mins at −78° C. After bubbling with argon, triphenylphosphine (510 mg, 1.94 mmol) was added to the solution, and the mixture was stirred for 2 hrs at −78° C. and further 3 hrs at rt. The mixture was concentrated in vacuo, and the residue was partially purified by silica gel column chromatography (hexane/AcOEt=4/1 to 2/1) to give crude lactol 11 (332 mg) as clear oil. The crude lactol (332 mg) was then dissolved in AcOEt (25 mL), and palladium hydroxide (20% on activated carbon, 180 mg) was added to the solution. The air in the reaction flask was replaced with hydrogen, and the reaction mixture was stirred overnight. The reagent was removed through filtration and the solvent was evaporated in vacuo to give crude triol 12 (150 mg) as pale-yellow oil. The crude triol 12 (150 mg) was dissolved in DCM/THF (30 mL/5 mL), and camphor sulfonic acid (130 mg) was added to the solution. The reaction mixture was stirred overnight and neutralized with sodium bicarbonate (100 mg), which was stirred for further 4 hrs. After filtration and evaporation, the residue was purified by silica gel column chromatography (1% methanol in DCM) to give bis-THF 1 (110 mg, 662 μmol, 68% for three steps) as white crystal. $^1$H-NMR (400 MHz, CDCl$_3$): δ 5.79 (d, J=5.3 Hz, 1H), 4.65-4.59 (m, 1H), 4.30-4.20 (m, 1H), 4.08-3.99 (m, 3H), 3.03-2.96 (m, 1H), 2.60 (t, J=5.8 Hz, 1H). $^{13}$C-NMR (100 MHz, CDCl$_3$): δ 128.31 (dd, J=254.6, 247.0 Hz), 108.31 (d, J=6.9 Hz), 74.71, 72.85 (t, J=30.0 Hz), 70.65 (d, J=6.1 Hz), 51.77 (dd, J=24.6, 17.9 Hz). $^{19}$F-NMR (376 MHz): δ−91.68 (ddt, J=247.4, 25.2, 12.8 Hz), −122.38 (d, J=247.4 Hz). $[α]_D^{20}$=+7.21 (c 0.68, CHCl$_3$). LRMS (CI): 167 (M+H)$^+$.

The THP-THF alcohol (n=2) may be prepared similarly starting from the ester of formula

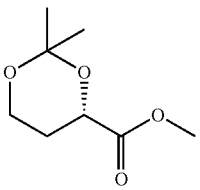

The fluorinated bis-THF ligand was activated by known a procedure using p-nitro phenyl chloroformate and coupled with amine isostere intermediates.

The compound:

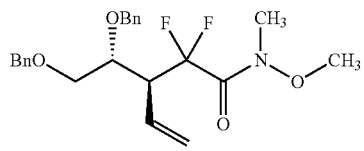 [SMILES: C=C[C@@H]([C@H](COCc1ccccc1)OCc1ccccc1)C(F)(F)C(=O)N(C)OC]

can be synthesized from:

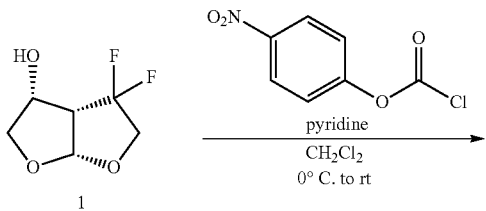

using similar synthetic methodology.

Synthesis of GRL-04810:

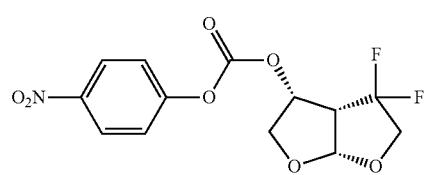

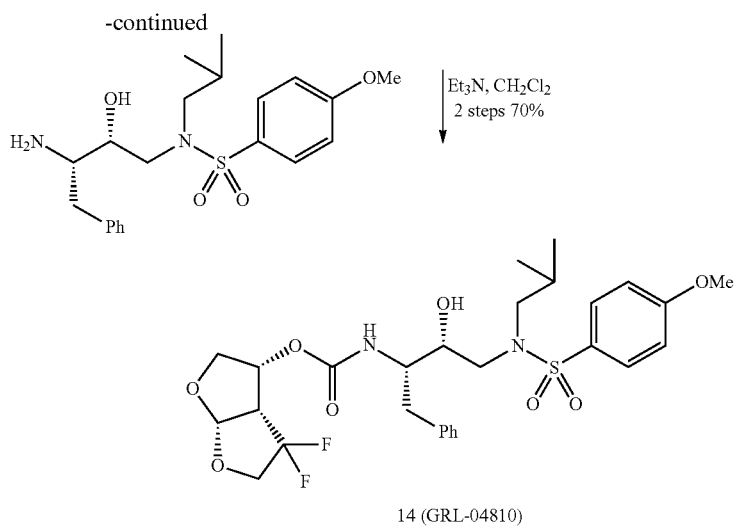

14 (GRL-04810)

Synthesis of Inhibitor 14 (GRL-04810):

A solution of bis-THF 1 (14.3 mg, 86.1 μmol) and pyridine (34.8 μL, 0.43 mmol) in dichloromethane (1.00 mL) was cooled down to 0° C., and 4-nitrophenyl chloroformate (53.7 mg, 0.26 mmol) was added to the solution in one portion. The temperature was raised to rt, and the mixture was stirred for 2 hr. The reaction was quenched with ethanol, and the solvent was removed in vacuo. The residue was partially purified by silica gel column chromatography (hexanes/AcOEt=5/1 to 2/1) to give crude carbonate 13 (25 mg). The half amount of the crude carbonate (12.5 mg) was added to a solution of the isostere (40 mg) and triethylamine (150 μL) in dichloromethane (2.00 mL). The reaction mixture was stirred for 3 days until all of the carbonate was consumed. After evaporating solvents, the residue was purified by silica gel column chromatography (1% methanol in DCM) to give inhibitor 14 (18.0 mg, 30.1 μmol, 83% for two steps).

$^1$H-NMR (400 MHz, CDCl$_3$): δ 7.69 (d, J=8.8 Hz, 2H), 7.30-7.20 (m, 5H), 6.99-6.96 (m, 2H), 5.77 (d, J=5.1 Hz, 1H), 5.35-5.29 (m, 1H), 5.00 (d, J=8.3 Hz, 1H), 4.08-3.68 (m, 10H), 3.15-2.75 (m, 7H), 1.86-1.79 (m, 1H), 0.91-0.85 (m, 6H). $^{13}$C-NMR (100 MHz, CDCl$_3$): δ 163.00, 154.84, 137.17, 129.68, 129.38, 128.48, 126.87 (t, J=267.2 Hz), 126.54, 114.27, 108.07, 72.67 (t, J=29.7 Hz), 72.26, 72.09, 71.10, 71.03, 58.68, 55.54, 55.13, 53.61, 50.05 (dd, J=18.8 Hz), 35.15, 27.18, 20.02, 19.75. $^{19}$F-NMR (376 MHz): δ −91.82 (ddt, J=248.2, 26.3, 15.0 Hz), −123.21 (d, J=248.2 Hz). LRMS (ESI): 599 (M+H)$^+$.

Synthesis of GRL-05010:

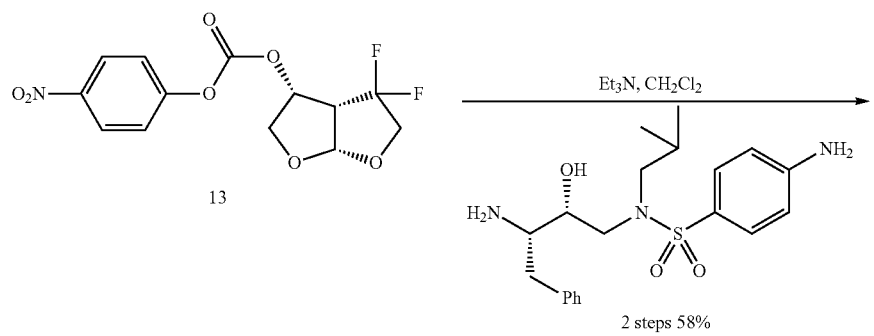

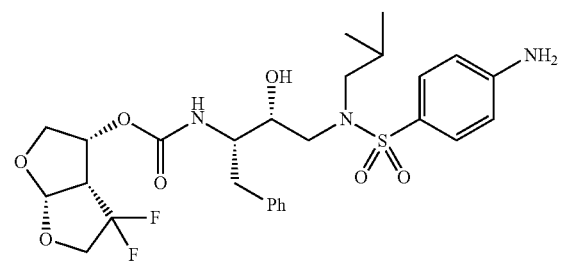

15 (GRL-05010)

Synthesis of Inhibitor 15 (GRL-05010):

Inhibitor 15 was obtained in 58% yield from bis-THF 1 through the same procedure when inhibitor 14 was obtained. $^1$H-NMR (400 MHz, CDCl$_3$): δ 7.53 (d, J=8.4 Hz, 2H), 7.32-7.21 (m, 5H), 6.68 (d, J=8.5 Hz, 2H), 5.78 (d, J=5.1 Hz, 1H), 5.35-5.28 (m, 1H), 4.76 (d, J=8.3 Hz, 1H), 4.23-3.70 (m, 12H), 3.15-2.72 (m, 7H), 1.86-1.73 (m, 1H), 0.93-0.87 (m, 6H). $^{13}$C-NMR (100 MHz, CDCl$_3$): δ 154.81, 150.66, 137.22, 129.42, 128.45, 126.85 (t, J=252.2 Hz), 126.50, 126.02, 114.01, 108.08, 72.67 (t, J=30.3 Hz), 72.32, 72.11, 71.03 (d, J=6.6 Hz), 58.77, 55.11, 53.67, 53.32, 50.08 (dd, J=27.5, 18.8 Hz), 35.20, 27.20, 20.05, 19.78. $^{19}$F-NMR (376 MHz): δ −91.79 (ddt, J=248.2, 26.3, 18.8 Hz), −123.24 (d, J=248.2 Hz). LRMS (ESI): 584 (M+H)$^+$.

Various intermediates may be prepared as follows:

Synthesis of Aryl Sulfonyl Chlorides

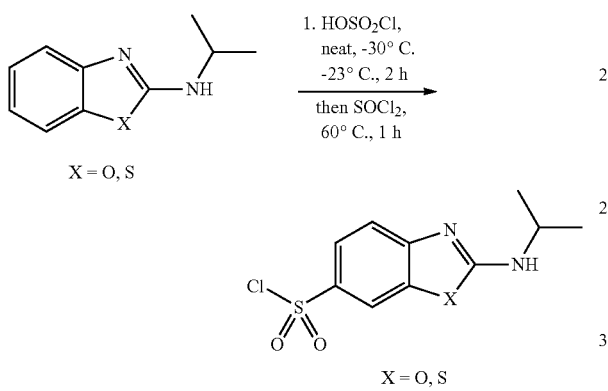

N-isopropylbenzo[d]oxazol-2-amine or N-isopropylbenzo[d]thiazol-2-amine were treated with chlorosulfonic acid (5.0 eq) at −30° C. The reaction was warmed to 23° C. and stirred at that temperature for 3 h. Thionyl chloride (2.0 eq) was added and the reaction was heated to 60° C. for 1 hr. The reaction was cooled to 0° C., diluted with ethyl acetate and washed with water. The organic layer was dried over sodium sulfate and concentrated under vacuum. The residue was dissolved in ethyl acetate and washed with a solution of saturated sodium bicarbonate. The crude sulfonyl chloride was used without further purification (85-90% yield).

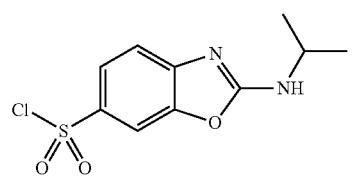 [SMILES: CC(C)Nc1nc2ccc(S(=O)(=O)Cl)cc2o1]

(16a): $^1$H NMR (400 MHz, Chloroform-d) δ 8.25 (s, 1H), 7.94 (d, J=8.7 Hz, 1H), 7.61 (d, J=8.7 Hz, 1H), 3.90 (bs, 1H), 1.38 (d, J=6.4 Hz, 6H).

(16b): $^1$H NMR (400 MHz, Chloroform-d) δ 7.92 (d, J=1.9 Hz, 1H), 7.89 (s, 3H), 5.63 (s, 1H), 4.17-4.10 (m, 1H), 1.38 (d, J=6.5 Hz, 6H).

Synthesis of the Hydroxyethyl Amine Isosteres

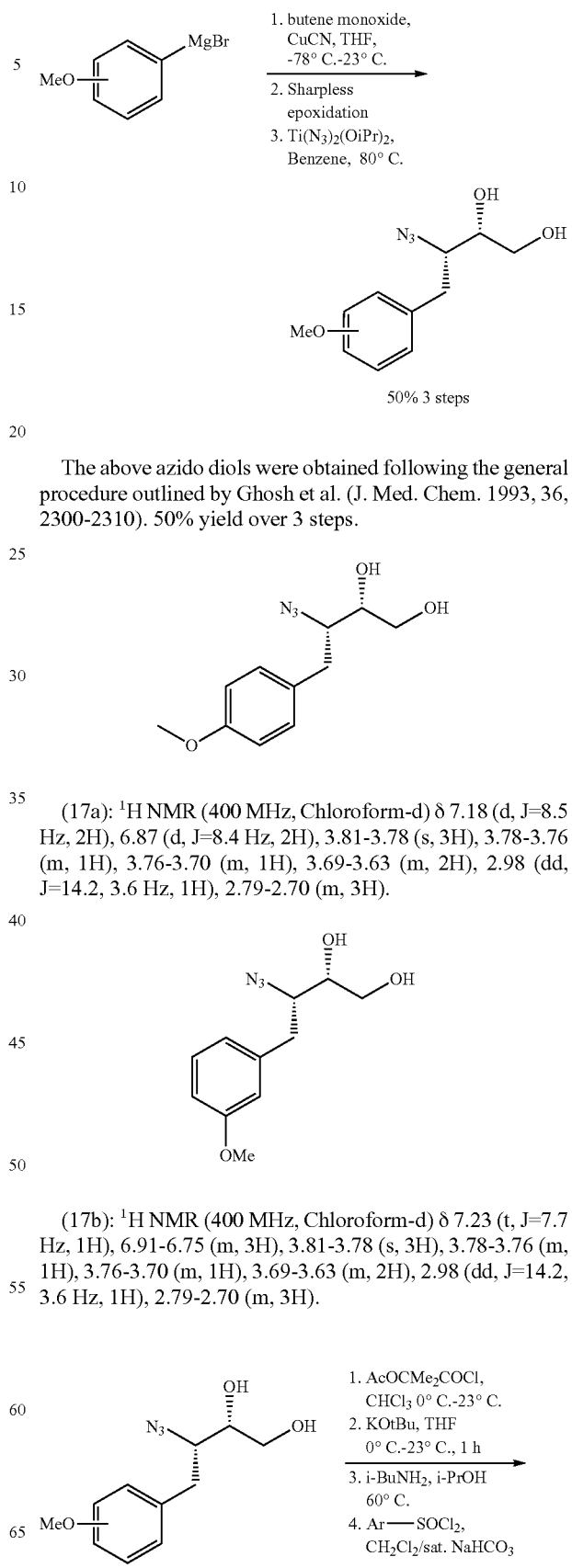

The above azido diols were obtained following the general procedure outlined by Ghosh et al. (J. Med. Chem. 1993, 36, 2300-2310). 50% yield over 3 steps.

(17a): $^1$H NMR (400 MHz, Chloroform-d) δ 7.18 (d, J=8.5 Hz, 2H), 6.87 (d, J=8.4 Hz, 2H), 3.81-3.78 (s, 3H), 3.78-3.76 (m, 1H), 3.76-3.70 (m, 1H), 3.69-3.63 (m, 2H), 2.98 (dd, J=14.2, 3.6 Hz, 1H), 2.79-2.70 (m, 3H).

(17b): $^1$H NMR (400 MHz, Chloroform-d) δ 7.23 (t, J=7.7 Hz, 1H), 6.91-6.75 (m, 3H), 3.81-3.78 (s, 3H), 3.78-3.76 (m, 1H), 3.76-3.70 (m, 1H), 3.69-3.63 (m, 2H), 2.98 (dd, J=14.2, 3.6 Hz, 1H), 2.79-2.70 (m, 3H).

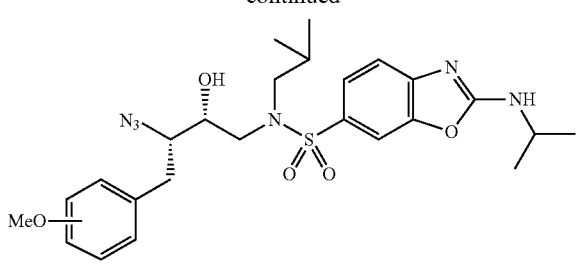

X = O, S
71-75% over 4 steps

The desired isosteres were obtained following the general procedures outlined by Ghosh et al. (J. Med. Chem. 1993, 36, 2300-2310) and Flentge et al. (US 2005-0131042). The desired isosteres were obtained in 71-75% yield over 4 steps.

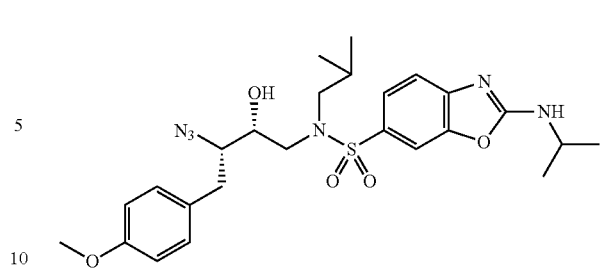

(18c): $^1$H NMR (400 MHz, Chloroform-d) δ 7.69 (s, 1H), 7.64 (dd, J=8.3, 1.7 Hz, 1H), 7.43 (d, J=8.3 Hz, 1H), 7.18 (d, J=8.6 Hz, 2H), 6.86 (d, J=8.6 Hz, 2H), 5.14 (d, J=7.9 Hz, 1H), 3.80 (s, 3H), 3.75 (d, J=7.2 Hz, 1H), 3.58-3.54 (m, 2H), 3.29-3.23 (dd, J=15.2, 9.3 Hz, 1H), 3.08-3.01 (m, 3H), 2.82-2.71 (m, 2H), 1.85-1.75 (m, 1H), 1.36 (d, J=6.5 Hz, 6H), 0.94 (d, J=6.6 Hz, 3H), 0.88 (d, J=6.6 Hz, 3H).

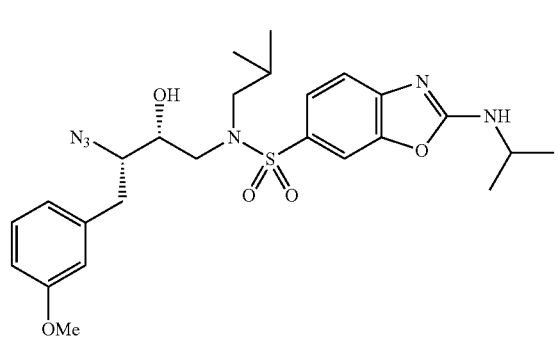 [SMILES: COc1cccc(C[C@H](N=[N+]=[N-])[C@H](O)CN(CC(C)C)S(=O)(=O)c2ccc3nc(NC(C)C)oc3c2)c1]

(18a): $^1$H NMR (400 MHz, Chloroform-d) δ 7.70 (d, J=1.5 Hz, 1H), 7.67-7.62 (d, J=8.1 Hz, 1H), 7.42 (d, J=8.3 Hz, 1H), 7.23 (t, J=7.7 Hz, 1H), 6.91-6.75 (m, 3H), 5.37 (d, J=7.7 Hz, 1H), 3.80-3.77 (s, 4H), 3.64-3.59 (m, 2H), 3.27 (dd, J=15.1, 9.4 Hz, 1H), 3.10-3.03 (m, 3H), 2.87-2.69 (m, 2H), 1.86-1.79 (m, 1H), 1.36 (d, J=6.5 Hz, 6H), 0.94 (d, J=6.6 Hz, 3H), 0.88 (d, J=6.6 Hz, 3H).

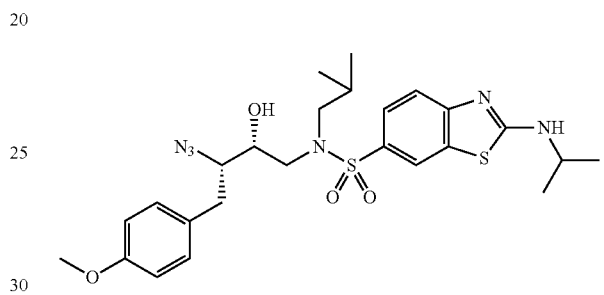

(18d): $^1$H NMR (400 MHz, Chloroform-d) δ 8.03 (d, J=1.7 Hz, 1H), 7.69 (dd, J=8.5, 1.9 Hz, 1H), 7.51 (d, J=8.5 Hz, 1H), 7.15 (d, J=8.6 Hz, 2H), 6.85 (d, J=8.6 Hz, 2H), 5.14 (d, J=7.9 Hz, 1H), 3.80 (s, 3H), 3.75 (d, J=7.2 Hz, 1H), 3.58-3.54 (m, 2H), 3.29-3.23 (dd, J=15.2, 9.3 Hz, 1H), 3.08-3.01 (m, 3H), 2.82-2.71 (m, 2H), 1.85-1.75 (m, 1H), 1.36 (d, J=6.5 Hz, 6H), 0.94 (d, J=6.6 Hz, 3H), 0.88 (d, J=6.6 Hz, 3H).

(18e)

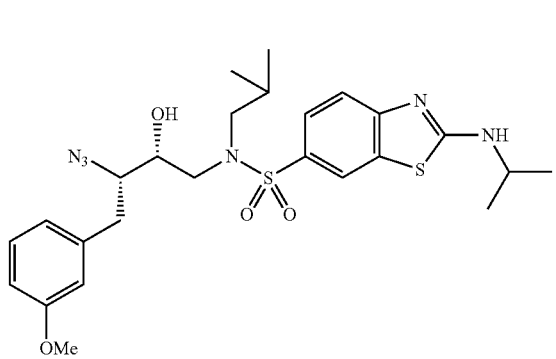 [SMILES: COc1cccc(C[C@H](N=[N+]=[N-])[C@H](O)CN(CC(C)C)S(=O)(=O)c2ccc3nc(NC(C)C)sc3c2)c1]

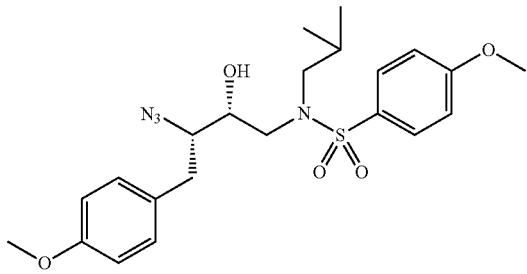

General Procedure for the Reduction of Azides 18a-18e:

Isosteres 18a-e were reduced following the Staudinger protocol (PPh$_3$, THF/H$_2$O, 23° C., 24 h) to give the corresponding amines 19a-19e, 19g (see 19g for NMR data).

(18b): $^1$H NMR (400 MHz, Chloroform-d) δ 8.04 (d, J=1.7 Hz, 1H), 7.69 (dd, J=8.5, 1.9 Hz, 1H), 7.55 (d, J=8.5 Hz, 1H), 7.22 (t, J=8.1 Hz, 1H), 6.86-6.79 (m, 3H), 5.97 (bs, 1H), 3.93 (bs, 1H), 3.79 (m, 5H), 3.66-3.60 (m, 1H), 3.27 (dd, J=15.2, 9.1 Hz, 1H), 3.13-3.03 (m, 3H), 2.86-2.74 (m, 2H), 1.86-1.80 (m, 1H), 1.34 (d, J=6.4 Hz, 6H), 0.93 (d, J=6.6 Hz, 3H), 0.88 (d, J=6.6 Hz, 3H).

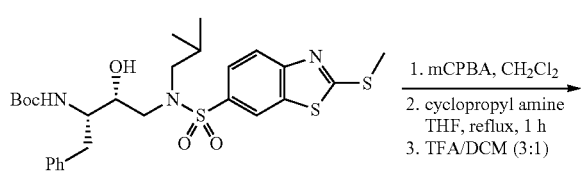

-continued

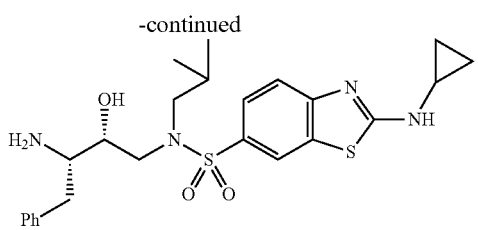

(19f): The above cyclopropyl amine isostere was obtained following the procedures outlined in J. Med. Chem. 2005, 48, 1965-1973. 84% yield over 3 steps. $^1$H NMR (400 MHz, Chloroform-d) δ 8.10 (s, 1H), 7.70 (d, J=8.5 Hz, 1H), 7.48 (d, J=8.5 Hz, 1H), 7.34-7.27 (m, 2H), 7.27-7.17 (m, 3H), 3.84-3.79 (m, 1H), 3.31-3.28 (m, 2H), 3.17-3.14 (m, 1H), 3.06 (dd, J=13.2, 8.2 Hz, 1H), 2.99-2.89 (m, 2H), 2.75-2.70 (m, 1H), 2.51 (dd, J=13.3, 10.1 Hz, 1H), 1.94-1.87 (m, 1H), 0.93 (d, J=6.6 Hz, 5H), 0.89 (d, J=6.6 Hz, 3H), 0.81-0.71 (m, 2H).

Synthesis of Fluorinated Isosteres:

The desired azido epoxide was obtained following the general procedures outlined by Ghosh et al. (J. Med. Chem. 1993, 36, 2300-2310) (using the appropriate stating materials).

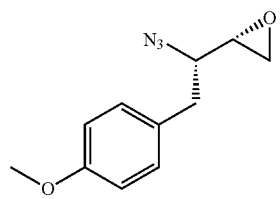 [SMILES: COc1ccc(C[C@H](N=[N+]=[N-])[C@H]2CO2)cc1]

(S)-2-((S)-1-azido-2-(4-methoxyphenyl)ethyl)oxirane (21): 84% over 2 steps. $^1$H NMR (400 MHz, Chloroform-d) δ 7.17 (d, J=8.4 Hz, 2H), 6.86 (d, J=8.4 Hz, 2H), 3.80 (s, 3H), 3.58-3.53 (m, 1H), 3.07-3.04 (m, 1H), 2.94 (dd, J=14.1, 4.6 Hz, 1H), 2.85-2.71 (m, 3H).

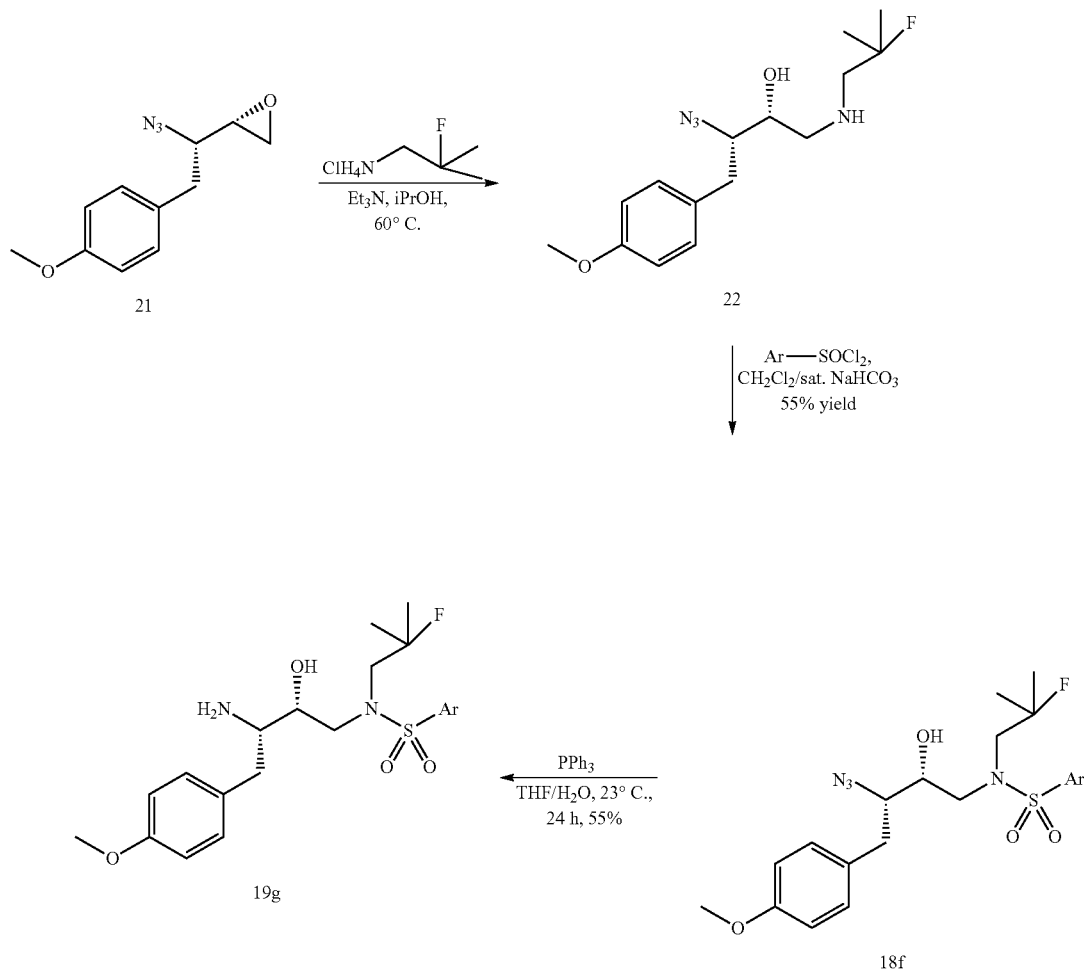

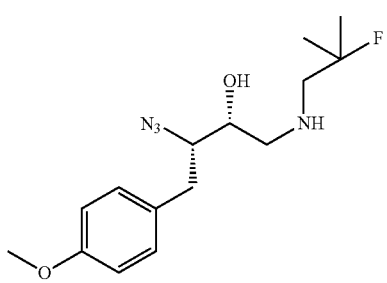 [SMILES: COc1ccc(C[C@H](N=[N+]=[N-])[C@H](O)CNCC(C)(C)F)cc1]

(2R,3S)-3-azido-1-(2-fluoro-2-methylpropylamino)-4-(4-methoxyphenyl)butan-2-ol (22)

To a solution of 2-fluoro-2-methylpropan-1-amine-HCl (2.0 eq) and triethyl amine (4.0 eq) in iPrOH was added an iPrOH solution of (S)-2-((S)-1-azido-2-(4-methoxyphenyl)ethyl)oxirane. The mixture was heated at 60° C. for 6 h. Upon completion the reaction mixture was concentrated then dissolved in ethyl acetate and washed with H$_2$O. The organic layer was combined washed with brine, dried over sodium sulfate and concentrated under vacuum. The residue was purified by flash chromatography. 50% yield. $^1$H NMR (400 MHz, Chloroform-d) δ 7.4 (d, J=8.4 Hz, 2H), 6.89 (d, J=8.4 Hz, 2H), 3.80 (s, 3H), 3.64-3.57 (m, 2H), 2.96-2.88 (m, 2H), 2.78-2.68 (m, 4H), 1.42 (d, J=3.1 Hz, 3H), 1.37 (d, J=3.1 Hz, 3H).

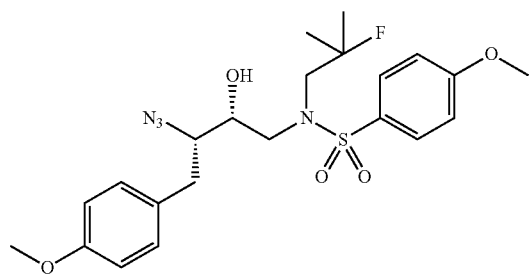

N-((2R,3S)-3-azido-2-hydroxy-4-(4-methoxyphenyl)butyl)-N-(2-fluoro-2-methylpropyl)-4-methoxybenzenesulfonamide (18f)

To a solution of amine 22 in dichloromethane was added 4-MeOPhSO$_2$Cl (1.2 eq) followed by a saturated solution of sodium bicarbonate (3.0 mL). The reaction was allowed to stir for 24 h. The reaction mixture was transferred to a separatory funnel and the organic layer was separated. The aqueous layer was washed with dichlormethane (2×). The organic layers were combined, dried over sodium sulfate, concentrated under vacuum and purified by flash chromatography. 55% yield. $^1$H NMR (400 MHz, Chloroform-d) δ 7.74 (d, J=8.9 Hz, 2H), 7.15 (d, J=8.6 Hz, 2H), 7.01 (d, J=8.9 Hz, 2H), 6.84 (d, J=8.6 Hz, 2H), 4.12-4.06 (m, 1H), 3.88 (s, 3H), 3.78 (s, 3H), 3.66-3.65 (m, 1H), 3.58-3.47 (m, 2H), 3.33 (dd, J=15.4, 9.1 Hz, 1H), 3.19-3.12 (m, 2H), 2.95 (dd, J=14.2, 3.4 Hz, 1H), 2.60 (dd, J=14.2, 10.0 Hz, 1H), 1.48 (d, J=21.7 Hz, 3H), 1.38 (d, J=21.4 Hz, 3H).

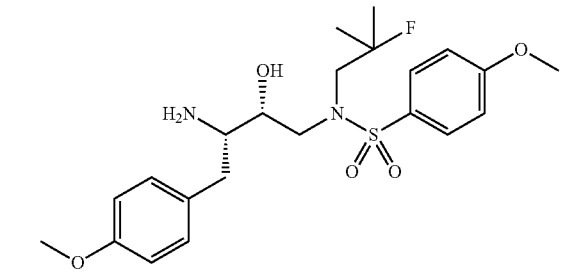

N-((2R,3S)-3-amino-2-hydroxy-4-(4-methoxyphenyl)butyl)-N-(2-fluoro-2-methylpropyl)-4-methoxybenzenesulfonamide (19g)

Azide 18f and triphenyl phosphine (1.2 eq) was dissolved in a solution of THF/H$_2$O (4:1). The reaction mixture was allowed to run for 24 h. Upon completion the reaction was diluted with ethyl acetate and extracted 3 times. The organic layers were combined and dried over anhydrous sodium sulfate. The solvent was removed under vacuum and the residue was purified using flash chromatography 60% ethylacetate/hexanes followed by 3% MeOH/CH$_2$Cl$_2$. 55% yield. $^1$H NMR (400 MHz, Chloroform-d) δ 7.74 (d, J=8.6 Hz, 2H), 7.09 (d, J=8.3 Hz, 2H), 6.98 (d, J=8.5 Hz, 2H), 6.82 (d, J=8.1 Hz, 2H), 3.93-3.90 (m, 1H), 3.85 (s, 3H), 3.77 (s, 3H), 3.51 (dd, J=27.4, 15.1 Hz, 1H), 3.41-3.20 (m, 3H), 3.04-3.01 (m, 1H), 2.88 (d, J=13.7 Hz, 1H), 2.33 (dd, J=13.4, 10.5 Hz, 1H), 1.46 (d, J=21.6 Hz, 3H), 1.37 (d, J=21.4 Hz, 3H).

General Procedure for the Synthesis of the HIV Protease Inhibitors:

The desired isostere (19a-f) is taken up in CH$_3$CN and cooled to 0° C. DIPEA (5 eq, excess) is added, followed by the corresponding activated fluorinated ligand. The resulting solution is stirred at room temperature until the reaction is complete. The solution is concentrated and the crude residue purified by flash column chromatography on silica gel to provide the desired inhibitor.

Biological Examples

Cells and Viruses.

MT-2 and MT-4 cells were grown in RPMI-1640-based culture medium supplemented with 10% fetal calf serum (FCS: JRH Biosciences, Lenexa, Md.), 50 unit/ml penicillin, and 100 μg/ml of kanamycin. The following HIV-1 viruses were employed for the drug susceptibility assay (see below): HIV-1LAI, HIV-1NL4-3, a clinical HIV-1 strain HIV-1ERS104pre isolated from a drug-naive patient with AIDS, (29), and six HIV-1 clinical isolates, which were originally obtained from patients with AIDS, who had received 9 to 11 anti-HIV-1 drugs over the past 32 to 83 months and were genotypically and phenotypically characterized as multi-PI-resistant HIV-1 variants. All primary HIV-1 strains were passaged once or twice in 3-day-old phytohemagglutinin activated peripheral blood mononuclear cells (PHA-PBM), and the culture supernatants were stored at −80° C. until use.

Antiviral Agents.

Saquinavir (SQV) was kindly provided by Roche Products Ltd. (Welwyn Garden City, United Kingdom) and Abbott Laboratories (Abbott Park, Ill.). Amprenavir (APV) was received as a courtesy gift from Glaxo-Wellcome, Research Triangle Park, N.C. Lopinavir (LPV) was kindly provided by Japan Energy Inc, Tokyo. Atazanavir (ATV) was a contribution from Bristol Myers Squibb (New York, N.Y.). Darunavir (DRV) was synthesized as previously described (30). 3'-Azido-2',3'-dioxythymidine (AZT) was purchased from Sigma-Aldrich (St. Louis, Mo.). Indinavir (IDV) was kindly provided by Merck Research Laboratories (Rahway, N.J.).

Drug Susceptibility Assay.

The susceptibility of HIV-1LAI to various drugs was determined as previously described with minor modifications. Briefly, MT-2 cells ($10^4$/ml) were exposed to 100 50% tissue culture infectious doses ($TCID_{50}$) of HIV-$1_{LAI}$ in the presence or absence of various concentrations of drugs in 96-well microculture plates and were incubated at 37° C. for 7 days. After 100 µl of the medium was removed from each well, 3-(4,5-dimetylthiazol-2-yl)-2,5-diphenyltetrazolium bromide (MTT) solution (10 µl, 7.5 mg/ml in phosphate-buffered saline) was added to each well in the plate, followed by incubation at 37° C. for 2 h. After incubation, to dissolve the formazan crystals, 100 µl of acidified isopropanol containing 4% (v/v) Triton X-100 was added to each well and the optical density measured in a kinetic microplate reader (Vmax; Molecular Devices, Sunnyvale, Calif.). All assays were performed in duplicate or triplicate. In some experiments, MT-2 cells were chosen as target cells in the MTT assay, since these cells undergo greater HIV-1-elicited cytopathic effects than MT-4 cells. To determine the sensitivity of primary HIV-1 isolates to drugs, phytohemagglutinin-stimulated peripheral blood mononuclear cells (PHA-PBMC) ($10^6$/ml) were exposed to 50 $TCID_{50}$ of each primary HIV-1 isolate and cultured in the presence or absence of various concentrations of drugs in 10-fold serial dilutions in 96-well microculture plates. In determining the drug susceptibility of certain laboratory HIV-1 strains, MT-4 cells were employed as target cells as previously described with minor modifications. In brief, MT-4 cells ($10^5$/ml) were exposed to 100 $TCID_{50}$ of drug-resistant HIV-1 strains in the presence or absence of various concentrations of drugs and were incubated at 37° C. On day 7 of culture, the supernatants were harvested and the amounts of p24 Gag protein were determined by using a fully automated chemiluminescent enzyme immunoassay system (Lumipulse F; Fujirebio Inc., Tokyo). Drug concentrations that suppressed the production of p24 Gag protein by 50% ($EC_{50}$) were determined by comparison with the p24 production level in drug-free control cell culture. All assays were performed in duplicate or triplicate. PHA-PBMs were derived from a single donor in each independent experiment. Thus, for obtaining the data, three different donors were recruited.

Generation of PI-Resistant HIV-1 Variants In Vitro.

MT-4 cells (105/ml) were exposed to HIV-$1_{NL4-3}$ (500 $TCID_{50}$) and cultured in the presence of various PIs at an initial concentration of its $EC_{50}$ value. Viral replication was monitored by the determination of the amount of p24 Gag produced by MT-4 cells. The culture supernatants were harvested on day 7 and used to infect fresh MT-4 cells for the next round of culture in the presence of increasing concentrations of each drug. When the virus began to propagate in the presence of the drug, the drug concentration was increased generally 2- to 3-fold. Proviral DNA samples obtained from the lysates of infected cells were subjected to nucleotide sequencing. This drug selection procedure was carried out until the drug concentration reached 5 µM (31-33). In the experiments for selecting drug-resistant variants, MT-4 cells were exploited as target cells since HIV-1 in general replicates at greater levels in MT-4 cells than in MT-2 cells.

Determination of Nucleotide Sequences.

Molecular cloning and determination of the nucleotide sequences of HIV-1 strains passaged in the presence of anti-HIV-1 agents were performed as described previously (31). In brief, high molecular-weight DNA was extracted from HIV-1-infected MT-4 cells by using the InstaGene Matrix (Bio-Rad Laboratories, Hercules, Calif.) and was subjected to molecular cloning, followed by sequence determination. The primers used for the first round of PCR with the entire Gag- and protease-encoding regions of the HIV-1 genome were LTR F1 (5'-GAT GCT ACA TAT AAG CAG CTG C-3'; SEQ ID NO: 13) and PR12 (5'-CTC GTG ACA AAT TTC TAC TAA TGC-3'; SEQ ID NO: 14). The first-round PCR mixture consisted of 1 µl of proviral DNA solution, 10 µl of Premix Taq (Ex Taq Version; Takara Bio Inc., Otsu, Japan), and 10 pmol of each of the first PCR primers in a total volume of 20 µl. The PCR conditions used were an initial 3 min at 95° C., followed by 35 cycles of 40 sec at 95° C., 20 sec at 55° C., and 2 min at 72° C., with a final 10 min of extension at 72° C. The first-round PCR products (1 µl) were used directly in the second round of PCR with primers LTR F2 (5'-GAG ACT CTG GTA ACT AGA GAT C-3'; SEQ ID NO: 15) and Ksma2.1 (5'-CCA TCC CGG GCT TTA ATT TTA CTG GTA C-3'; SEQ ID NO: 16) under the PCR conditions of an initial 3 min at 95° C., followed by 35 cycles of 30 sec at 95° C., 20 sec at 55° C., and 2 min at 72° C., with a final 10 min of extension at 72° C. The second-round PCR products were purified with spin columns (MicroSpin S-400 HR columns; Amersham Biosciences Corp., Piscataway, N.J.), cloned directly, and subjected to sequencing with a model 3130 automated DNA sequencer (Applied Biosystems, Foster City, Calif.).

Determination of Replication Kinetics of GRL-04810- and GRL-05010-Resistant HIV-$1_{NL4-3}$ Variants and Wild-Type HIV-$1_{NL4-3}$.

GRL-04810- and GRL-05010-resistant variants were obtained at passages 18 and 10, respectively and propagated in fresh MT-4 cells without the drugs for 7 days, and viral stocks were stored at −80° C. until use. MT-4 cells ($3\times10^5$) were exposed to the wild-type HIV-$1_{NL4-3}$ preparation or HIV-$1_{NL4-3}$ preparations selected with GRL-04810 over 18 passages and GRL-05010 over 10 passages, designated as HIV-$1_{GRL-04810}{}^R{}_{P18}$ and HIV-$1_{GRL-05010}{}^R{}_{P10}$, respectively, containing 10 ng/ml p24, in 6-well culture plates for 3 hours, such MT-4 cells were subsequently washed with fresh medium, divided into 3 fractions and each cultured with or without each compound (final concentration of MT-4 cells $10^4$/ml, and drug concentrations 0.01 µM and 0.001 µM). The amounts of p24 were measured every two days for up to 7 days.

Determination of Partition and Distribution Coefficients of GRL-04810 and GRL-05010 Using the Shake-Flask Method.

On day −1 of the experimental setting, saturation of 1-octanol ($CH_3(CH_2)_6CH_2OH$) (Nacalai Tesque, Kyoto, Japan) water and tris-buffered saline (10X working solution 20 mM Tris, pH 7.4 and 0.9% NaCl, Sigma-Aldrich, St. Louis, Mo.) took place. Four different flasks were used: One containing 50 ml of water plus 100 ml of 1-octanol, the second flask contained 1-octanol saturated with water adding 50 ml of 1-octanol and 100 ml of water. The same ratios and volumes were kept for 1-octanol saturated with tris-buffer and tris-buffer saturated with 1-octanol. The flasks were sealed and placed into a room temperature bio shaker for 24 hours at 90 revolutions per minute. Simultaneously, dilutions of GRL-04810, GRL-05010 and DRV were performed from a 20 mM DMSO stock to a final concentration of 100 µM using dH$_2$O, tris-buffered saline and 1-octanol as solvents. Successive dilutions were made to obtain concentrations of 10 µM, 1 µM and 0.1 µM. A standard curve was generated on a light spectrophotometer (DU Series 700, Beckman Coulter Fullerton, Calif.) at 230 nanometer absorbances.

On day 1 of the experiment, the lipid and liquid interfaces were separated, and compounds were diluted again from 20 mM DMSO to 100 µM using the 1-octanol, water and Tris-buffered saline obtained from the shake-flask assay. The resulting diluted compounds were then added to separate serum tubes containing equal proportions of 1-octanol and water, and 1-octanol and Tris-buffered saline. The solution was handshaken for 5 minutes and then centrifuged at 3,500 rpm and room temperature for 20 minutes. Finally, the compounds were recovered from the 1-octanol, Tris-buffer and water interfaces and then measured on a light spectrophotometer.

The values for logP and logD were obtained by applying the following mathematical formulas:

$$\log Pow = \frac{[\ ]n-\text{octanol}}{[\ ]\text{water}}$$

$$\log D = \frac{[\text{compound}]\text{octanol}}{[\text{compound}]\text{ionized} + [\text{compound}]\text{neutral}}$$

Determination of Apparent Permeability Blood Brain Barrier Coefficient of GRL-04810 and GRL-05010 Using a Novel In Vitro Model.

A novel in vitro BBB model (BBB Kit™, PharmaCo-Cell Ltd. Nagasaki, Japan), incorporating a triple culture of rat-derived astrocytes, pericytes and monkey-derived endothelial cells (34) was used to determine the apparent permeability BBB coefficient (Papp cm/s) of GRL-04810, GRL-05010, AZT, IDV, SQV, LPV, ATV, DRV, caffeine and sucrose.

The BBB Kit™ was kept at −80° C. until thawing on day 0 of the experiments. Nutritional medium was added to both brain and blood sides of the wells. This solution consists of DMEM F-12 medium with FCS 10% v/v, heparin 100 µg/ml, basic fibroblast growth factor (bFGF) 1.5 ng/ml, insulin 5 µg/ml, transferrin 5 µg/ml, sodium selenite 5 ng/ml, hydrocortisone 500 nM and gentamycin 50 µg/ml. Fresh medium was added 3 hours after thawing following the manufacturer's instructions, and 24 hours later. The plates were incubated at 37° C. until day 4 of the experiment when the condition of astrocytes was checked under a light microscope. Following this, the integrity of the collagen-coated membrane was verified by the measurement of the transendothelial electrical resistance (TEER) using an ohmmeter provided by the manufacturer. As TEER increases over the days reaching a culprit between days 4 and 6 of the experiment, determinations were done during this period. Membranes were tested individually and those collagen-coated membranes displaying TEER values greater than 150 Ω/cm$^2$ were deemed suitable for the execution of the drug BBB penetration assay. Detailed information regarding the components of the BBB Kit as well as its mechanisms can be seen by accessing the manufacturer's website http://www.pharmacocell.co.jp/en/bbb/index_e.html.

Once the conditions of cell viability and membrane integrity were met, drug dilutions were performed from 20 mM DMSO stocks of GRL-04810, GRL-05010, AZT, IDV, SQV, LPV, ATV and DRV, while caffeine and sucrose were used as positive and negative controls, respectively. Standard curves were generated for each compound on a light spectrophotometer as previously described. 100 µM of each compound was added to the luminal (blood side) of the wells, incubated at 37° C. for 30 minutes and then, the amount of drug that crossed the in vitro BBB was collected and measured under a light spectrophotometer at 230 nanometer absorbances.

Papp was calculated using the following mathematical formula:

$$Papp(\text{cm/s}) = \frac{VA}{A \times [C]\text{luminal}} \times \frac{\Delta[C]\text{abluminal}}{\Delta t}$$

Where: VA=volume of the abluminal chamber (0.9 cm$^3$)
A=membrane surface area (0.33 cm$^2$)
[C] luminal=initial luminal compound concentration (µM)
Δ[C] abluminal=abluminal compound concentration (µM)
Δt=time of the experiment (seconds)

Determination of Antiviral Activity of GRL-04810, GRL-05010 and DRV Recovered from the Brain Side of the BBB Assay.

Each drug that successfully crossed the brain interface in the BBB assay described above was harvested and designated as GRL-04810$^{brain}$, GRL-05010$^{brain}$, DRV$^{brain}$, AZT$^{brain}$, IDV$^{brain}$, and SQV$^{brain}$. The susceptibility of HIV-1$_{LAI}$ and HIV-1$_{ERS104pre}$ to GRL-04810$^{brain}$, GRL-05010$^{brain}$, DRV$^{brain}$, AZT$^{brain}$, IDV$^{brain}$, SQV$^{brain}$ was then determined in MTT assay using MT-2 cells or p24 assay employing PHA-PBMs as described in the drug susceptibility assay section. The assay was carried out using 10, 100, 1000 and 10000 times-diluted brain-side stocks of compounds.

Structural Interactions of GRL-04810 and GRL-05010 with Wild-Type HIV-1 Protease.

Molecular models of the interactions of GRL-04810 and GRL-05010 with wild-type HIV-1 protease were generated as described: The coordinates of the structure of a reference compound, GRL-0519, with HIV-1 protease were obtained from the protein data bank (PDB ID 3OK9, http://www.rcsb.org/). GRL-0519 shares a structural similarity with GRL-04810, and its structure was modified to generate the molecular model of interactions of GRL-04810 and HIV-1 protease. The complex was energy-minimized using OPLS-2005 force-field as implemented in Maestro™ (version 9.3, Schrödinger, LLC, New York, N.Y., 2012). A model of the interactions of GRL-05010 with HIV-1 protease was obtained in a similar fashion using the crystal structure of darunavir with protease (PDB ID 2IEN) as a reference. Visualization, analyses of the models and figures depicting structural interactions were generated using Maestro™.

Antiviral Activity of GRL-04810 and GRL-05010 Against HIV-1LAI.

The antiviral activities of GRL-04810 and GRL-05010 that contain two fluorine atoms in the bis-THF moiety against a variety of HIV-1 isolates were examined. It was found that GRL-04810 and GRL-05010 were highly active in vitro against a wild-type laboratory HIV-1 strain, HIV-$1_{LAI}$, with $EC_{50}$ values of 0.0008 and 0.003 μM, respectively, as examined using the MTT assay with MT-2 as target cells, while FDA-approved PIs (SQV, LPV, ATV, APV and DRV) displayed $EC_{50}$ values ranging from 0.005 to 0.03 μM (Table 1). Cytotoxicity was seen for GRL-04810 and GRL-05010 only at high concentrations with $CC_{50}$ values of 17.5 and 37.0 μM; and the selectivity indexes proved to be high for GRL-04810 with 21,875, while GRL-05010 scored a moderate selectivity index of 12,333 (Table 1).

TABLE 1

Antiviral activity of GRL-04810 and GRL-05010 against HIV-$1_{LAI}$ and their cytotoxicity.

| Compound | $EC_{50}$ (μM) HIV-$1_{LAI}$ | $CC_{50}$ (μM) | Selectivity Index* |
|---|---|---|---|
| SQV | 0.021 ± 0.001 | 17.7 ± 3.4 | 843 |
| LPV | 0.020 ± 0.001 | 26.8 ± 0.9 | 1,340 |
| ATV | 0.005 ± 0.001 | 28.6 ± 0.9 | 5,720 |
| APV | 0.03 ± 0.001 | >100 | >3,333 |
| DRV | 0.005 ± 0.001 | >100 | >20,000 |
| GRL-04810 | 0.0008 ± 0.0002 | 17.5 ± 0.9 | 21,875 |
| GRL-05010 | 0.003 ± 0.001 | 37.0 ± 0.4 | 12,333 |

MT-2 cells ($10^4$/ml) were exposed to 100 $TCID_{50}$ of HIV-$1_{LAI}$ and cultured in the presence of various concentrations of each PI, and the $EC_{50}$ values were determined by the MTT assay. All assays were conducted in duplicate, and the data shown represent mean values derived from the results of three independent experiments. *Each selectivity index denotes a ratio of 50% cytotoxicity ($CC_{50}$) to $EC_{50}$ against HIV-$1_{LAI}$.

GRL-04810 and GRL-05010 Exert Potent Activity Against Highly PI-Resistant Clinical HIV-1 Isolates.

Previously, was reported (35) the isolation of highly multi-PI-resistant primary HIV-1 strains, HIV-$1_{MDR/B}$, HIV-$1_{MDR/C}$, HIV-$1_{MDR/G}$, HIV-$1_{MDR/TM}$, HIV-$1_{MDR/JSL}$ and HIV-$1_{MDR/MM}$ from patients with AIDS, who had failed then-existing anti-HIV regimens after receiving 9 to 11 anti-HIV-1 drugs over 32 to 83 months. These primary strains contained 9 to 14 amino acid substitutions in the protease-encoding region, which have reportedly been associated with HIV-1 resistance against various PIs (see the legend to Table 2). The $EC_{50}$ values of SQV, LPV, ATV, and APV against clinical multi-drug-resistant HIV-1 strains were significantly higher than those against a wild-type clinical HIV-1 isolate, HIV-$1_{ERS104pre}$, as examined in the assay employing PHA-PBMs as target cells using p24 production inhibition as an endpoint. However, GRL-04810 and GRL-05010 exerted quite potent antiviral activity and their $EC_{50}$ values against those clinical variants were substantially low, varying from 0.002 μM to 0.021 μM (Table 2). GRL-04810 and GRL-05010 proved to be more potent against all the six multi-drug-resistant clinical HIV-1 variants examined, compared to all the currently available approved PIs examined. The two compounds were comparably or more potent against the variants in comparison with DRV (Table 2).

TABLE 2

Antiviral activity of GRL-04810 and GRL-05010 against multi-drug resistant clinical isolates in PHA-PBMCs.

| Virus[a] | $EC_{50}$ (μM) | | | | | | |
|---|---|---|---|---|---|---|---|
| | SQV | LPV | ATV | APV | DRV | GRL-04810 | GRL-05010 |
| HIV-$1_{ERS104pre}$ (X4) | 0.0039 ± 0.0001 | 0.033 ± 0.003 | 0.0021 ± 0.0001 | 0.0295 ± 0.0004 | 0.004 ± 0.001 | 0.0023 ± 0.0001 | 0.0027 ± 0.0003 |
| HIV-$1_{MDR/B}$ (X4) | 0.35 (90) ± 0.01 | >1 (>33) | 0.45 (214) ± 0.07 | 0.49 (15) ± 0.05 | 0.021 (5) ± 0.001 | 0.014 (7) ± 0.001 | 0.011 (3) ± 0.001 |
| HIV-$1_{MDR/C}$ (X4) | 0.31 (78) ± 0.02 | >1 (>33) | 0.43 (204) ± 0.01 | 0.21 (7) ± 0.02 | 0.005 (1) ± 0.001 | 0.002 (1) ± 0.001 | 0.002 (1) ± 0.001 |
| HIV-$1_{MDR/G}$ (X4) | 0.039 (10) ± 0.002 | >1 (>33) | 0.042 (19) ± 0.001 | 0.31 (11) ± 0.08 | 0.014 (4) ± 0.009 | 0.004 (2) ± 0.001 | 0.004 (1) ± 0.001 |
| HIV-$1_{MDR/TM}$ (X4) | 0.10 (25) ± 0.04 | >1 (>33) | 0.056 (24) ± 0.007 | 0.328 (12) ± 0.001 | 0.03 (9) ± 0.01 | 0.004 (2) ± 0.001 | 0.004 (2) ± 0.001 |
| HIV-$1_{MDR/JSL}$ (R5) | 0.53 (133) ± 0.01 | >1 (>33) | >1 (>476) | 0.630 (22) ± 0.009 | 0.025 (5) ± 0.002 | 0.021 (10) ± 0.004 | 0.020 (7) ± 0.0002 |
| HIV-$1_{MDR/MM}$ (R5) | 0.11 (27) ± 0.01 | >1 (>33) | 0.081 (38) ± 0.008 | 0.27 (9) ± 0.01 | 0.010 (3) ± 0.001 | 0.002 (1) ± 0.001 | 0.003 (1) ± 0.001 |

[a]The amino acid substitutions identified in the protease-encoding region compared to the consensus type B sequence cited from the Los Alamos database include L63P in HIV-$1_{ERS104pre}$; L10I, K14R, L33I, M36I, M46I, F53L, K55R, I62V, L63P, A71V, G73S, V82A, L90M, I93L in HIV-$1_{MDR/B}$; L10I, I15V, K20R, L24I, M36I, M46L, I54V, I62V, L63P, K70Q, V82A, L89M in HIV-$1_{MDR/C}$; and L10I, V11I, T12E, I15V, L19I, R41K, M46L, L63P, A71T, V82A, L90M in HIV-$1_{MDR/G}$; L10I, K14R, R41K, M46L, I54V, L63P, A71V, V82A, L90M, I93L in HIV-$1_{MDR/TM}$; L10I, L24I, I33F, E35D, M36I, N37S, M46L, I54V, R57K, I62V, L63P, A71V, G73S, V82A in HIV-$1_{MDR/JSL}$; L10I, K43T, M46L, I54V, L63P, A71V, V82A, L90M, Q92K in HIV-$1_{MDR/MM}$. HIV-$1_{ERS104pre}$ served as a source of wild-type HIV-1. The $EC_{50}$ values were determined by using PHA-PBMs as target cells and the inhibition of p24 Gag protein production by each drug was used as an endpoint. The numbers in parentheses represent the fold changes of $EC_{50}$ values for each isolate compared to the $EC_{50}$ values for wild-type HIV-$1_{ERS104pre}$. All assays were conducted in duplicate or triplicate, and the data shown represent mean values (±1 standard deviations) derived from the results of three independent experiments. PHA-PBMs were derived from a single donor in each independent experiment.
GRL-04810 and GRL-05010 are potent against PI-selected laboratory HIV-1 variants.

GRL-04810 and GRL-05010 also were examined against a variety of HIV-1$_{NL4-3}$ variants selected in vitro with each of four FDA-approved PIs (SQV, LPV, ATV, and APV). Such variants were selected by propagating HIV-1$_{NL4-3}$ in the presence of increasing concentrations of each PI (up to 5 µM) in MT-4 cells and those variants had acquired various PI resistance-associated amino acid substitutions in the protease-encoding region of the viral genome (see the legend to Table 3). Those variants were designated as HIV-1$_{SQV}{}^R{}_{5\mu M}$, HIV-1$_{LPV}{}^R{}_{5\mu M}$, HIV-1$_{ATV}{}^R{}_{5\mu M}$, and HIV-1$_{APV}{}^R{}_{5\mu M}$, depending on the drug each of the variant was selected against. Each of the variants was highly resistant to the very PI, against which the variant was selected, and showed a significant resistance with EC$_{50}$ values of >1 µM. GRL-04810 and GRL-05010 were generally as active against HIV-1$_{SQV}{}^R{}_{5\mu M}$, HIV-1$_{LPV}{}^R{}_{5\mu M}$, and HIV-1$_{ATV}{}^R{}_{5\mu M}$ as was DRV (Table 3) when the absolute EC$_{50}$ values were compared (Table 3). As in the case of DRV, the two compounds were less potent against HIV-1$_{APV}{}^R{}_{5\mu M}$ with the EC$_{50}$ values of 0.43 and 0.56 µM, respectively, presumably due to their structural resemblance to APV.

HIV-1$_{NL4-3}$, in MT-4 cells in the presence of increasing concentrations of each of the two drugs as previously described (31). HIV-1$_{NL4-3}$ was exposed to GRL-04810 with an initial concentration of 0.003 µM and underwent 25 passages when the virus had acquired an ability to replicate in the presence of a 26-fold-increased concentration of GRL-04810 (0.080 µM). Selection assay was also carried out for GRL-05010 starting at 0.003 µM. (FIG. 2) and HIV-1$_{NL4-3}$ attained an ability to replicate in the presence of 0.037 µM GRL-05010 by passage 15.

Judging from the amounts of p24 Gag protein secreted into the culture medium, the replicative capacity of HIV-1$_{NL4-3}$ at passages 25 and 15 for GRL-04810 and GRL-05010, respectively, was generally maintained. It was compared whether the emergence of resistance-associated amino acid substitutions in GRL-04810- and GRL-05010-exposed HIV-1$_{NL4-3}$ was delayed in comparison with the emergence of resistant variants against two commercially available FDA-approved PIs (LPV and DRV). The protease-encoding region of proviral DNA isolated from MT-4 cells was cloned and sequenced at passages 5, 10, 15, and 20 during the GRL-04810 selection,

TABLE 3

Antiviral activity of GRL-04810 and GRL-05010 against laboratory PI-resistant HIV-1 variants and GRL-04810- and GRL-05010-exposed HIV-1 variants.

| Virus[a] | EC$_{50}$ (µM) | | | | | | |
|---|---|---|---|---|---|---|---|
| | SQV | LPV | ATV | APV | DRV | GRL-04810 | GRL-05010 |
| HIV-1$_{NL4-3}$ | 0.037 ± 0.002 | 0.035 ± 0.005 | 0.0047 ± 0.0001 | 0.081 ± 0.001 | 0.004 ± 0.001 | 0.0005 ± 0.0005 | 0.0037 ± 0.0001 |
| HIV-1$_{SQV}{}^R{}_{5\mu M}$ | >1 (>25) | >1 (>25) | >1 (>250) | 0.435 (5) ± 0.001 | 0.04 (10) ± 0.01 | 0.13 (260) ± 0.05 | 0.046 (13) ± 0.001 |
| HIV-1$_{LPV}{}^R{}_{5\mu M}$ | 0.025 (1) ± 0.005 | >1 (>25) | 0.033 (8) ± 0.001 | 0.033 (1) ± 0.005 | 0.032 (8) ± 0.001 | 0.03 (66) ± 0.01 | 0.03 (8) ± 0.02 |
| HIV-1$_{ATV}{}^R{}_{5\mu M}$ | 0.46 (12) ± 0.02 | >1 (>25) | >1 (>250) | >1 (>13) | 0.05 (13) ± 0.01 | 0.02 (36) ± 0.01 | 0.04 (12) ± 0.02 |
| HIV-1$_{APV}{}^R{}_{5\mu M}$ | 0.09 (2) ± 0.04 | >1 (>25) | 0.66 ± 0.02 | >1 (>13) | 0.51 (128) ± 0.03 | 0.43 (860) ± 0.02 | 0.56 (187) ± 0.03 |
| HIV-1$_{GRL04810}{}^R{}_{P18}$ | 0.032 (1) ± 0.005 | 0.37 (11) ± 0.02 | 0.325 (81) ± 0.004 | >1 (>13) | 0.041 (11) ± 0.001 | 0.033 (66) ± 0.003 | 0.039 (13) ± 0.005 |
| HIV-1$_{GRL05010}{}^R{}_{P10}$ | 0.036 (1) ± 0.003 | 0.375 (11) ± 0.005 | 0.095 (24) ± 0.035 | >1 (>13) | 0.037 (10) ± 0.003 | 0.029 (58) ± 0.001 | 0.036 (10) ± 0.001 |

[a]The amino acid substitutions identified in the protease-encoding region compared to the wild-type HIV-1$_{NL4-3}$ include L10F, V32I, M46I, I54M, A71V, I84V in HIV-1$_{APV}{}^R{}_{5\mu M}$; L23I, E34Q, K43I, M46I, I50L, G51A, L63P, A71V, V82A, T91A in HIV-1$_{ATV}{}^R{}_{5\mu M}$; L10F, M46I, I54V, V82A in HIV-1$_{LPV}{}^R{}_{5\mu M}$; and L10I, G48V, I54V, A71V, I84V, L90M in HIV-1$_{SQV}{}^R{}_{5\mu M}$. MT-4 cells (10$^5$/ml) were exposed to 100 TCID$_{50}$s of each HIV-1, and the inhibition of p24 Gag protein production by each drug was used as an endpoint. The numbers in parentheses represent the fold changes of EC$_{50}$ values for each isolate compared to the EC$_{50}$ values for wild-type HIV-1$_{NL4-3}$. All assays were conducted in duplicate or triplicate, and the data shown represent mean values (±1 standard deviations) derived from the results of two or three independent experiments. In addition, GRL-04810- and GRL-05010-resistant variants selected in vitro were used for antiviral activity determination assays. Time point viruses were harvested at passages 18 and 10, respectively. Washing steps were performed to remove the remaining compounds from the viral stocks, and compound-free viruses were obtained for the experiment. 5 commercially available protease inhibitors were used as controls. Absolute values are given plus the fold changes relative to the baseline EC$_{50}$ for each compound. By passage 18, three amino acid substitutions A28S, L33F and V82I were identified in HIV-1$_{GRL04810}{}^R{}_{P18}$; by passage 10, M46I, I50V, N38K and M36I were detected in HIV-1$_{GRL05010}{}^R{}_{P10}$. Assays were performed in duplicate and the average values (with 1 S.D.) are shown.
GRL-04810 and GRL-0510 are moderately active against highly DRV-resistant HIV-1 variants.

The antiviral activity of the two compounds against DRV-resistant variants, which we previously selected out in vitro against DRV, was also examined. These variants were generated using the mixture of 8 highly multi-PI-resistant clinical isolates as a starting HIV-1 population and were selected with increasing concentrations of DRV. GRL-04810 and GRL-05010 exhibited slightly decreased activity against variants selected with DRV over 10 and 20 passages (EC$_{50}$: 0.03-0.034 µM for the former and 0.026-0.043 µM for the latter, Supplementary Table 1), while DRV was less active against HIV-1$_{DRV}{}^R{}_{P20}$ than the two compounds with an EC$_{50}$ value of 0.174 µM (Supplementary Table 1).

In Vitro Selection of HIV-1 Variants Resistant to GRL-04810 and GRL-05010

It was attempted to select HIV-1 variants with GRL-04810 and GRL-05010 by propagating a laboratory HIV-1 strain, and passages 5, 10, and 15 for GRL-05010. HIV-1$_{NL4-3}$ exposed to GRL-04810, by passage 20, had acquired L33F and V82I in 15 of 22 clones and A28S in 5 clones. HIV-1$_{NL4-3}$ exposed to GRL-05010 had acquired amino acid substitutions M46I and I50V by passage 15 in all 24 clones examined, while N38K was detected in 8 of 24 clones and M36I in 3 clones (FIG. 3).

GRL-04810- and GRL-05010-Resistant HIV-1$_{NL4-3}$ Variants Maintain Robust Replicative Activity.

The replication kinetics of HIV-1$_{GRL-04810}{}^R{}_{P18}$, HIV-1$_{GRL-05010}{}^R{}_{P10}$, and the wild-type HIV-1$_{NL4-3}$ were determined using replication kinetic assays as previously described (31). HIV-1$_{NL4-3}$ well replicated in the presence of 0.001 µM of each of the two compounds, but delayed in starting to replicate or failed to replicate in the presence of 0.01 μM of each compound in the 7-day replication kinetic assay (FIG. 4). However, HIV-1$_{GRL-04810}{}^{R}{}_{P18}$, and HIV-1$_{GRL-05010}{}^{R}{}_{P10}$ robustly replicated in the presence of 0.001 and 0.01 μM of each of the two compounds (FIG. 4).

GRL-04810 and GRL-05010 Remain Active Against the Variants Selected with GRL-04810 and GRL-05010.

It was then attempted to determine the impact of the amino acids substitutions identified in HIV-1$_{GRL-04810}{}^{R}{}_{P18}$, and HIV-1$_{GRL-05010}{}^{R}{}_{P10}$. Five commercially available protease inhibitors (SQV, LPV, ATV, APV and DRV) were used as controls. GRL-04810 and GRL-05010 generally remained active against HIV-1$_{GRL-04810}{}^{R}{}_{P18}$, and HIV-1$_{GRL-05010}{}^{R}{}_{P10}$ with $EC_{50}$ values ranging from 0.029 μM to 0.039 μM. SQV was active against the two variants HIV-1$_{GRL-04810}{}^{R}{}_{P18}$ and HIV-1$_{GRL-05010}{}^{R}{}_{P10}$ with narrow $EC_{50}$ ranges from 0.032 to 0.036 μM; while LPV displayed values significantly higher (0.37 and 0.375 μM) than those of GRL-04810 and GRL-05010. ATV was moderately active against the HIV-1$_{GRL-05010}{}^{R}{}_{P10}$ variant (0.095 μM), while the absolute $EC_{50}$ values of GRL-04810 and GRL-05010 were generally lower than the $EC_{50}$ values of ATV against those variants. As for DRV, the values against the resistant variants to GRL-04810 and GRL-05010 were 0.041 and 0.037 μM, respectively. However, APV was not active against all the selected variants examined ($EC_{50}$ values of >1 μM), presumably due to its structural resemblance to the two PIs used for the selection (Table 3).

GRL-04810 and GRL-05010 Show Favorable Lipophilicity Indexes for their Partition and Distribution Coefficients.

The addition of fluorine atoms is generally expected to confer greater lipophilicity on nucleoside analogs and certain compounds (37-39). Thus, we determined the partition (logP) and distribution coefficients (logD) of GRL-04810 and GRL-05010. 1-Octanol, organic alcohol, and water were used for logP determination, while tris-buffered saline (pH 7.4) and water were utilized for logD determination. Prior to obtaining the actual values, a standard curve was generated as a reference and drug concentrations attained for each compartment (1-octanol, water and tris-buffered saline) were measured on a light spectrophotometer (at 230 nanometer absorbance) as previously described by Rak et al. (40). Of note, GRL-04810 reached the highest concentration in the octanol lipid interface (72 μM) versus 14.09 μM for GRL-05010 and 11.89 μM for DRV (Table 4). GRL-04810 appeared most lipophilic with a logD value of −0.29, representing a 4-fold greater logD value as compared to that of DRV (−1.03), in a view that the more negative the logD value is, the less lipophilic the substance is estimated to be (40). GRL-05010 was found to have a logD value (−1.01) comparable to that of DRV.

TABLE 4

Partition (log P) and distribution (log D) coefficients of GRL-04810, GRL-05010, and DRV using the shake flask method.

| Compound | Concentration (μM) | | | | Log P$_{OW}$ (Octanol/Water) | Log D$_{Oct/Tris}$ pH 7.40 |
| --- | --- | --- | --- | --- | --- | --- |
| | in water | in tris buffer | in octanol$^{(a)}$ | in octanol$^{(b)}$ | | |
| GRL-04810 | 99.78 | 42.32 | 70.00 | 72.00 | −0.14 | −0.29 |
| GRL-05010 | 94.55 | 49.84 | 18.70 | 14.09 | −0.83 | −1.01 |
| DRV | 81.49 | 48.77 | 15.50 | 11.89 | −0.63 | −1.03 |

The partition (logP) and distribution coefficients (logD) of GRL-04810 and GRL-05010 were determined. DRV was used as a control. N-octanol, an organic alcohol, and water were used for logP determination, while tris buffer and water were utilized for the logD assay. Prior to the retrieval of actual values a standard curve was generated as a reference. The drug concentrations for each compartment (octanol, water and tris buffer) were measured at 230 nanometer absorbances using a light spectrophotometer. Assay was performed following the OECD guidelines for testing of chemicals "Partition coefficient (n-octanol-water): shake flask method", adopted by the council on 27 Jul. 1995.$^{(a)}$ n-octanol used for logP$_{OW}$ determination;$^{(b)}$ n-octanol used for logD assay. The formulas $$Pow = \frac{[\ ]n - \text{octanol}}{[\ ]\text{water}}$$

and $$\log D = \frac{[\text{compound}]\text{octanol}}{[\text{compound}]\text{ionized} + [\text{compound}]\text{neutral}}$$

were used for calculations.

GRL-04810 and GRL-05010 Penetrate Well Across the Blood-Brain Barrier In Vitro.

It was also attempted to evaluate whether GRL-04810 and GRL-05010 had optimal apparent permeability blood-brain barrier (BBB) coefficients employing an in vitro model using a triple cell co-culture system with rat astrocytes and pericytes and monkey endothelial cells. This model (BBB Kit™) is thought to represent an in vitro BBB model for drug transport assays, permitting an adequate cross-talk of the cell lines involved and provide a way to test an apparent passage of small molecules across the BBB as previously described by Nakagawa et al. (41). AZT, IDV, SQV, LPV, ATV DRV, GRL-04810, or GRL-05010 was added to the luminal interface (termed the "blood side") of microtiter culture wells under the optimal conditions for trans-endothelial electrical resistance (TEER) determination. The concentrations of each compound that permeated into the abluminal interface (termed "brain side") were determined using a spectrophotometer, 30 min after the addition of each drug to the wells. As shown in Table 5, the amounts of caffeine and sucrose, serving as the most and least lipophilic substances, in the abluminal interface were 6.60 and 0.03 μM, respectively. AZT, IDV, SQV, LPV, ATV, and DRV were also used as controls in the assay, giving the amounts of 1.50, 2.42, 0.33, 0.94, 1.02 and 0.65 μM, respectively. By contrast, GRL-04810 and GRL-05010 yielded greater concentrations with 3.16 and 4.08 μM in the abluminal interface of the microtiter culture wells.

TABLE 5

Estimation of the apparent blood brain barrier (BBB) permeability coefficient using an in vitro model.

| Compound | Initial luminal tracer concentration (μM) | Final abluminal tracer concentration (μM) | Papp (10$^{-6}$ cm/s) |
| --- | --- | --- | --- |
| AZT | 100 | 1.50 ± 0.12 | 22.7 ± 1.9 |
| IDV | 100 | 2.42 ± 0.12 | 36.7 ± 1.7 |
| SQV | 100 | 0.33 ± 0.03 | 4.9 ± 0.4 |
| LPV | 100 | 0.94 ± 0.05 | 14.2 ± 0.7 |
| ATV | 100 | 1.02 ± 0.10 | 15.4 ± 1.4 |
| DRV | 100 | 0.65 ± 0.23 | 9.9 ± 4.2 |
| GRL-04810 | 100 | 3.16 ± 0.48 | 47.8 ± 8.8 |
| GRL-05010 | 100 | 4.08 ± 0.65 | 61.8 ± 12.1 |
| caffeine (positive control) | 100 | 6.60 | 100 |
| sucrose (negative control) | 100 | 0.03 ± 0.005 | 0.33 ± 0.13 |

In the in vitro model using a triple co-culture of rat astrocytes, pericytes and monkey endothelial cells, AZT, IDV, SQV, LPV, ATV, DRV, GRL-04810, GRL-05010 (all 100 µM) and the positive and negative controls (caffeine and sucrose) were added to the luminal interface (termed blood side) of duplicate wells. The mathematical formula used for the calculation of Papp is described in Materials and Methods. Results show average values ±1 S.D. of duplicated determinations.

The apparent permeability coefficient (Papp), referred to as a brain uptake index (BUI), is a way to determine the penetration efficiency of a compound across a BBB model quantitatively and qualitatively (42). The Papp values of GRL-04810 ($47.8 \times 10^{-6}$ cm/s) and GRL-05010 ($61.8 \times 10^{-6}$ cm/s) were significantly greater than that of DRV ($9.9 \times 10^{-6}$ cm/s) and those of other antiviral drugs tested: AZT ($22.7 \times 10^{-6}$ cm/s), IDV ($36.7 \times 10^{-6}$ cm/s), SQV ($4.9 \times 10^{-6}$ cm/s), LPV ($14.2 \times 10^{-6}$ cm/s) and ATV ($15.4 \times 10^{-6}$ cm/s). Compounds with apparent permeability coefficients greater than $20 \times 10^{-6}$ cm/s are thought to have reasonably efficient penetration across BBB, those with values of 10 to $20 \times 10^{-6}$ cm/s have a moderate degree of penetration, whereas those with values lower than $10 \times 10^{-6}$ cm/s do not well penetrate BBB (41). GRL-04810 and GRL-05010 Recovered from the Brain Interface in the BBB Model Retains Antiviral Activity Greater than that of DRV.

Finally, it was attempted to examine whether the drug concentrations penetrated into the abluminal interface ("brain side") in the BBB Kit™ as described above, had sufficient activity to suppress the replication of HIV-1 in vitro. Each drug that successfully crossed the brain interface in the BBB assay was harvested and designated as GRL-04810$^{brain}$, GRL-05010$^{brain}$, DRV$^{brain}$, AZT$^{brain}$, IDV$^{brain}$, and SQV$^{brain}$. The susceptibility of HIV-1$_{LAI}$ and HIV-1$_{ERS104pre}$ to GRL-04810$^{brain}$, GRL-05010$^{brain}$, DRV$^{brain}$, AZT$^{brain}$, IDV$^{brain}$, SQV$^{brain}$ was then determined in MTT assay using MT-2 cells or p24 assay employing PHA-PBMs as described in the drug susceptibility assay section. In the assay, we 10-fold serially diluted the original "brain side" preparation containing GRL-04810 (3.16 µM) (designated GRL-04810$^{brain}$) and determined their antiviral suppression levels. The 10-fold diluted GRL-04810$^{brain}$ (containing 0.316 µM) suppressed HIV-1$_{LAI}$ replication by 94%, whereas 100-fold diluted GRL-04810$^{brain}$ (containing 0.0316 µM) by 45%. The 10-fold diluted GRL-05010$^{brain}$ (containing 0.408 µM) suppressed HIV-1$_{LAI}$ replication by 91%, whereas 100-fold diluted GRL-05010$^{brain}$ (containing 0.0316 µM) by 73%. However, the suppression levels of all other preparations, DRV$^{brain}$, AZT$^{brain}$, IDV$^{brain}$, and SQV$^{brain}$ examined were less than those of GRL-04810$^{brain}$ and GRL-05010$^{brain}$ (FIG. 5A). When PHA-activated PBMCs and a treatment-naïve clinical isolate HIV-1$_{ERS104pre}$ were used in the drug susceptibility assay, virtually the same antiviral profiles of GRL-04810$^{brain}$ and GRL-05010$^{brain}$ were observed (FIG. 5B).

Molecular Interactions of GRL-04810 and GRL-05010 with Wild-Type HIV-1 Protease

Molecular models of the interactions of GRL-04810 and GRL-05010 with wild-type HIV-1 protease were generated. A bird's eye view of GRL-04810 bound to protease is shown in FIG. 6A. The interactions of DRV with HIV-1 protease seen in a crystal structure (FIG. 6B) share key interactions with both GRL-04810 and GRL-05010 as follows. Analysis of the model structure revealed that both oxygen atoms present in the bis-THF group of GRL-04810 have polar interactions with the backbone nitrogens of Asp29 and Asp30 in the S2 site of the protease (FIG. 6C). The O-methoxy oxygen has a polar interaction with the backbone NH of Asp30' in the S2' site of the protease. GRL-04810 maintains polar interactions with Gly27 and Asp25, as well as with Ile50 and Ile50' through a bridging water molecule. The oxygens in the bis-THF group of GRL-05010 also exhibit polar interactions with Asp29 and Asp30 in the S2 site of protease (FIG. 6D). Polar interactions with Gly27, the catalytic Asp25, and the bridging water molecule are also seen for GRL-05010. Even though both GRL-04810 and GRL-05010 form polar interactions with Asp30' in the S2' site of the protease, there is a subtle difference due to the different chemical moiety present in the P2' of these inhibitors. The O-methoxy oxygen forms a polar contact with the backbone NH of Asp30', while the NH nitrogen of GRL-05010 forms a polar contact with the backbone carboxyl of Asp30'. The fluoride atoms in the bis-THF group of GRL-04810 and GRL-05010 fill the otherwise empty cavity towards the HIV-1 protease flap.

REFERENCES FOR EXAMPLES

Amano M, Koh Y, Das D, Li J, Leschenko S, Wang Y F, Boross P I, Weber I T, Ghosh A K, Mitsuya H. 2007. A novel bis-tetrahydrofuranylurethane-containing nonpeptidic protease inhibitor (PI), GRL-98065, is potent against multiple-PI-resistant human immunodeficiency virus in vitro. Antimicrob. Agents Chemother. 51:2143-2155.

Ide K, Aoki M, Amano M, Koh Y, Yedidi R S, Das D, Leschenko S, Chapsal B, Ghosh A K, Mitsuya H. 2011. Novel HIV-1 protease inhibitors (PIs) containing a bicyclic P2 functional moiety, tetrahydropyrano-tetrahydrofuran, that are potent against multi-PI-resistant HIV-1 variants. Antimicrob. Agents Chemother. 55:1717-1727.

Tojo Y, Koh Y, Amano M, Aoki M, Das D, Kulkarni S, Anderson D D, Ghosh A K, Mitsuya H. 2010. Novel protease inhibitors (PIs) containing macrocyclic components and 3(R),3a(S),6a(R)-bis-tetrahydrofuranylurethane that are potent against multi-PI-resistant HIV-1 variants in vitro. Antimicrob. Agents Chemother. 54:3660-3670.

Nakagawa S, Deli M A, Kawaguchi H, Shimizudani T, Shimono T, Kittel A, Tanaka K, Niwa M. 2009. A new blood-brain barrier model using primary rat brain endothelial cells, pericytes and astrocytes. Neurochem. Int. 54:253-263.

Yoshimura K, Kato R, Kavlick M F, Nguyen A, Maroun V, Maeda K, Hussain K A, Ghosh A K, Gulnik S V, Erickson J W, Mitsuya H. 2002. A potent human immunodeficiency virus type 1 protease inhibitor, UIC-94003 (TMC-126), and selection of a novel (A28S) mutation in the protease active site. J. Virol. 76:1349-1358.

Koh Y, Amano M, Towata T, Danish M, Leshchenko-Yashchuk S, Das D, Nakayama M, Tojo Y, Ghosh A K, Mitsuya H. 2010. In vitro selection of highly darunavir-resistant and replication-competent HIV-1 variants by using a mixture of clinical HIV-1 isolates resistant to multiple conventional protease inhibitors. J. Virol. 84:11961-11969.

Bright T V, Dalton F, Elder V L, Murphy C D, O'Connor N K, Sandford G 2013. A convenient medical-microbial method for developing fluorinated pharmaceuticals. Org. Biomol. Chem. 11:1135-1142.

Karppi J, Akerman S, Akerman K, Sundell A, Nyyssonen K, Penttila I. 2007. Adsorption of drugs onto a pH responsive poly(N,N dimethyl aminoethyl methacrylate) grafted anion-exchange membrane in vitro. Int. J. Pharm. 29:7-14.

Peng Liu, Sharon A, Chu C K. 2008. Fluorinated nucleosides: synthesis and biological implication. J. Fluor. Chem. 129:743-766.

Rak J, Dejlova B, Lampova H, Kaplanek R, Matejicek P, Cigler P, Kral V. 2013. On the solubility and lipophilicity of metallacarborane pharmacophores. Mol. Pharm. 10:1751-1759.

Nakagawa S, Deli M A, Nakao S, Honda M, Hayashi K, Nakaoke R, Kataoka Y, Niwa M. 2007. Pericytes from brain microvessels strengthen the barrier integrity in primary cultures of rat brain endothelial cells. Cell Mol. Neurobiol. 27:697-694.

The following embodiments are provided, the numbering of which is not to be construed as designating levels of importance:

Embodiment 1 relates to a compound of the formula

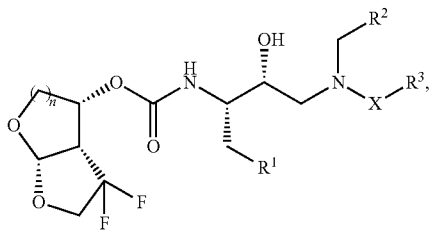

or a pharmaceutically acceptable salt thereof, wherein
n is the integer 1 or 2;
$R^1$ is phenyl which is unsubstituted or which bears a fluoro, hydroxymethyl, methoxy or 2-(morpholin-4-yl)ethoxy substituent at the 3- or 4-position, or is 3,5-difluorophenyl;
$R^2$ is 2-propyl or 2-fluoro-2-propyl; and
—X—$R^3$ is selected from the group consisting of —$SO_2$—$R^3$, —C(O)—N(R)—$R^3$, —NH—$SO_2$—$R^3$, and —NH—C(O)—$OR^3$;
in which R is selected from the group consisting of (1-6C) alkyl, aryl, heteroaryl, aryl(1-6C)alkyl or heteroaryl(1-6C) alkyl, each of which is optionally substituted;
$R^3$ is selected from the group consisting of (1-6C)alkyl, aryl, heteroaryl, aryl(1-6C)alkyl or heteroaryl(1-6C)alkyl, each of which is optionally substituted.

Embodiment 2 relates to the compound of Embodiment 1, wherein —X—$R^3$ is —$SO_2$—$R^3$.

Embodiment 3 relates to the compound of Embodiments 1-2, wherein $R^3$ is selected from the group consisting of 4-aminophenyl, 4-methoxyphenyl, 4-hydroxymethylphenyl, 3-fluoro-4-methoxyphenyl, 4-amino-3-fluorophenyl, 3,4-methylenedioxyphenyl, benzoxazole-6-yl bearing a methyl, methylsulfonyl, dimethylamino or —NH—$R^4$ group at the 2-position; benzothiazole-6-yl bearing a methyl, methylsulfonyl, dimethylamino or —NH—$R^4$ group at the 2-position; and benzimidazole-5-yl bearing a methyl or —NH—$R^4$ group at the 2-position; and $R^4$ is selected from the group consisting of methyl, prop-2-yl, cyclopropyl, isobutyl, tert-butyl, cyclobutyl, cyclopentyl, cyclohexyl, piperidin-4-yl, 1-methylpiperidin-4-yl, 1-(prop-2-yl) piperidin-4-yl and 1-cyclopentylpiperidin-4-yl.

Embodiment 4 relates to the compound of Embodiments 3, wherein $R^3$ is selected from the group consisting of 4-aminophenyl, 4-methoxyphenyl, and 3-fluoro-4-methoxyphenyl.

Embodiment 5 relates to the compound of Embodiment 3, wherein $R^3$ is 2-(prop-2-ylamino)benzoxazole-6-yl.

Embodiment 6 relates to compound of Embodiment 3, wherein $R^3$ is benzothiazole-6-yl bearing a methylsulfonyl, dimethylamino, 2-(prop-2-ylamino)-, cyclopropylamino, isobutylamino, tert-butylamino, cyclohexylamino, piperidin-4-ylamino, or 1-cyclopentylpiperidin-4-ylamino group at the 2-position.

Embodiment 7 relates to the compound of Embodiments 1-6, wherein $R^2$ is 2-propyl.

Embodiment 8 relates to the compound of Embodiments 1-7, wherein $R^1$ is phenyl, 3-methoxyphenyl or 4-methoxyphenyl.

Embodiment 9 relates to the compound of Embodiment 8, wherein $R^1$ is phenyl.

Embodiment 10 relates to the compound of Embodiments 1-9, wherein R is hydrogen or methyl.

Embodiment 11 relates to the compound of Embodiments 1-10, wherein n is the integer 1.

Embodiment 12 relates to the compound of Embodiment 1-11, wherein n is the integer 2.

Embodiment 13 relates to the compound of Embodiment 1-12, wherein n is the integer 1 or 2; $R^1$ is phenyl, 3-methoxyphenyl or 4-methoxyphenyl; $R^2$ is 2-propyl or 2-fluoro-2-propyl; —X—$R^3$ is —$SO_2$—$R^3$; and $R^3$ is selected from the group consisting of 4-aminophenyl, 4-methoxyphenyl, 3-fluoro-4-methoxyphenyl; 2-(prop-2-ylamino)-benzoxazole-6-yl; and benzothiazole-6-yl bearing a methylsulfonyl, dimethylamino, 2-(prop-2-yl-amino)-, cyclopropylamino, isobutylamino, tert-butylamino, cyclohexylamino, piperidin-4-ylamino, or 1-cyclopentylpiperidin-4-ylamino group at the 2-position.

Embodiment 14 relates to the compound of Embodiments 1-13, selected from the group consisting of:

a.

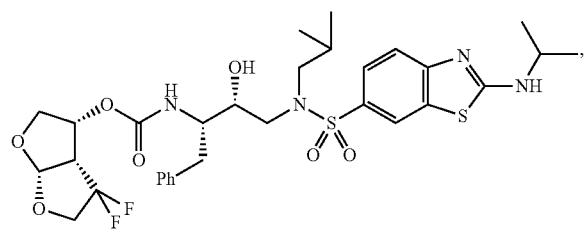

b.

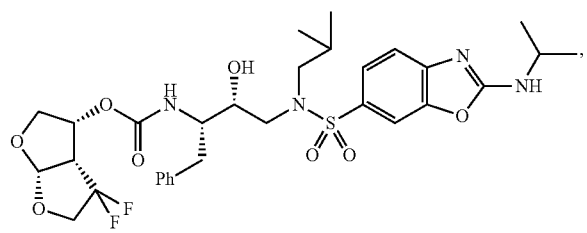

c.

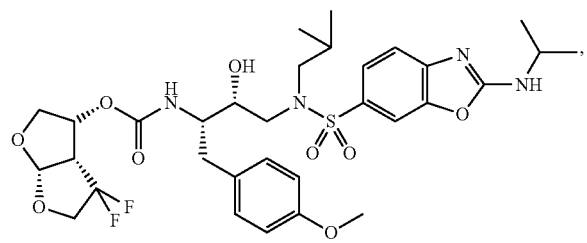

d.

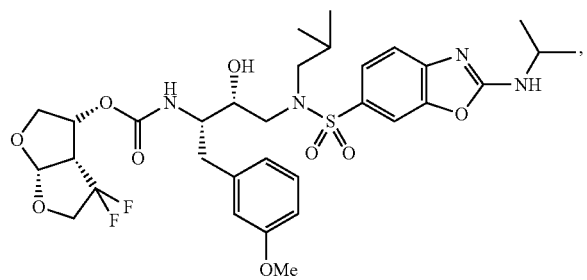

-continued
e.
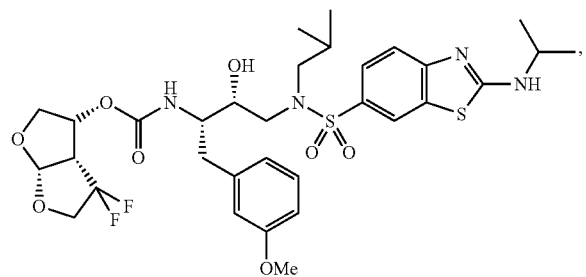
f.
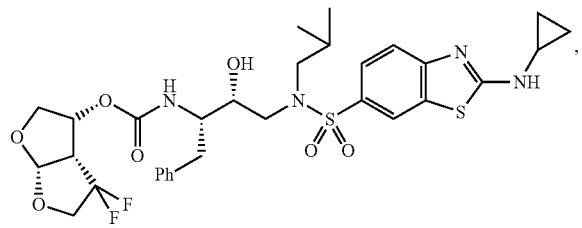
g.
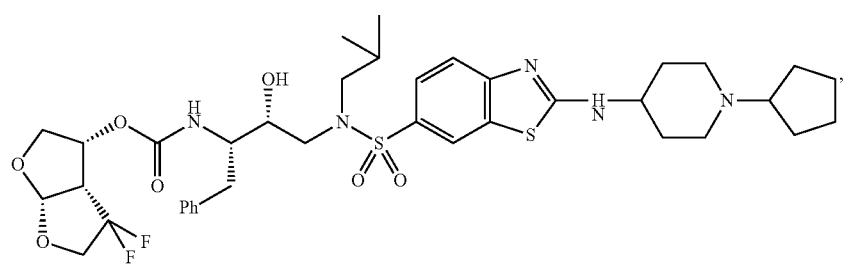
h.
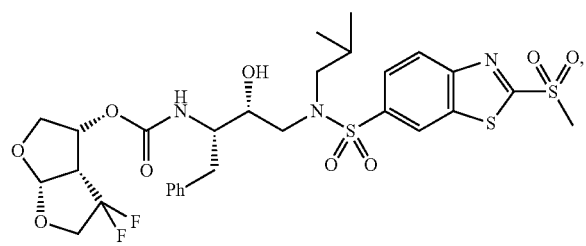
i.
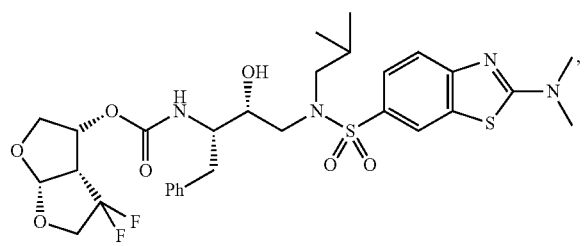
j.
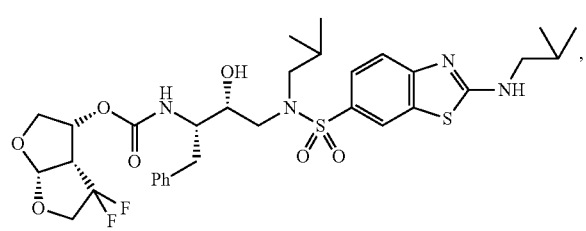
k.
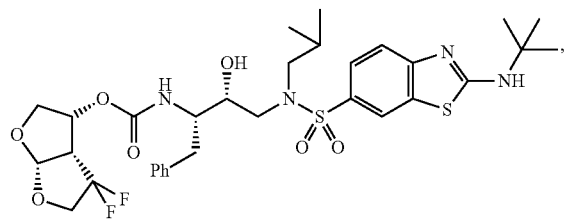
l.
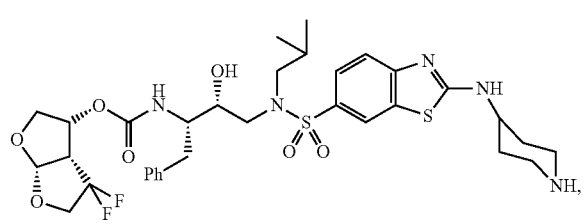
m.
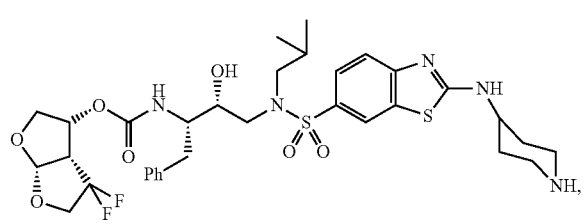
n.
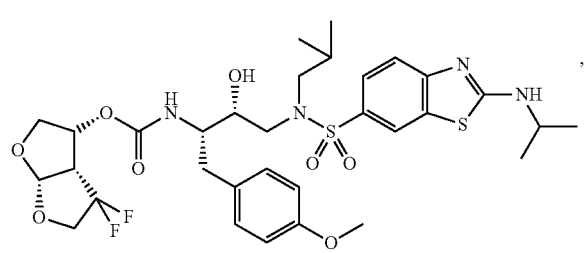
o.
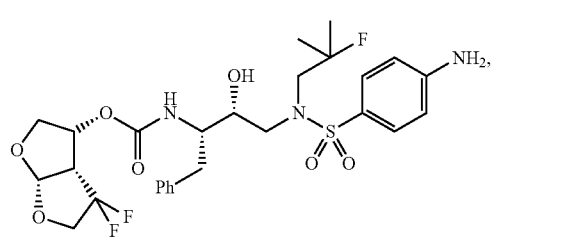

-continued
p.
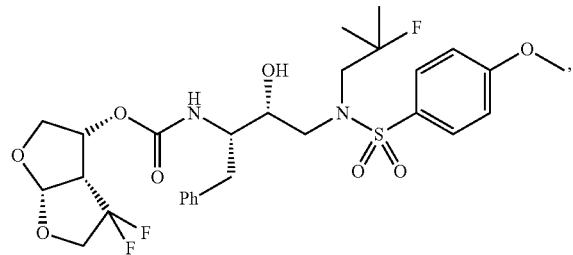
q.
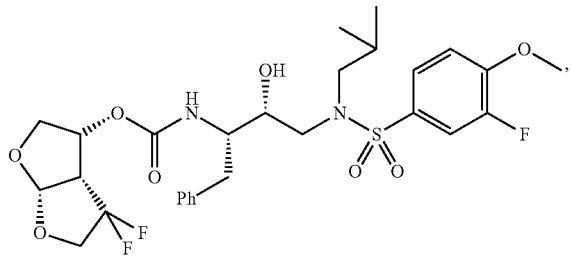
r.
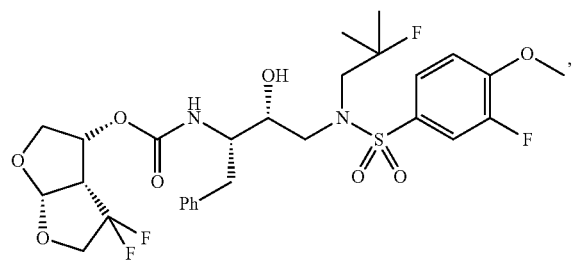
s.
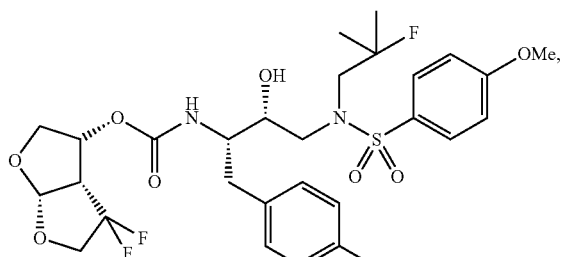
t.
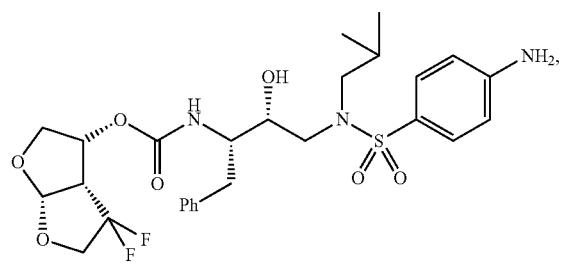
u.
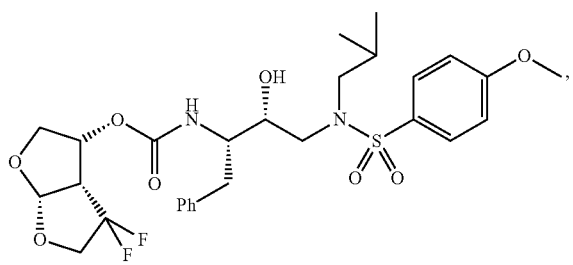
v.
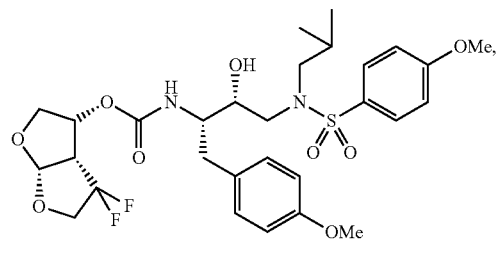
w.
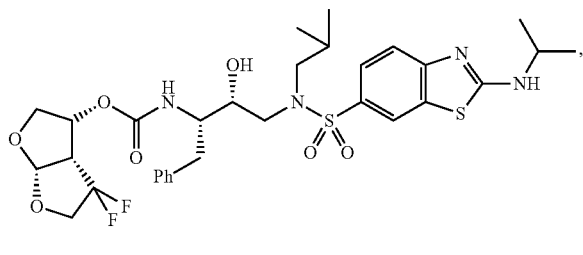
x.
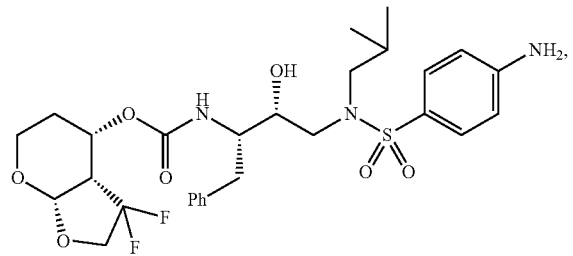
y.
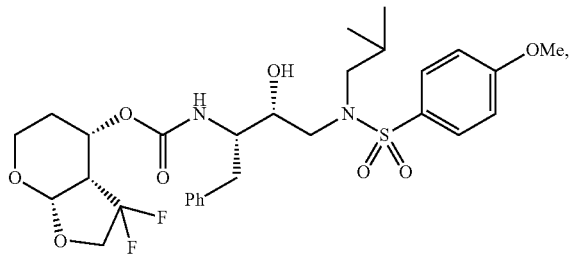

z.
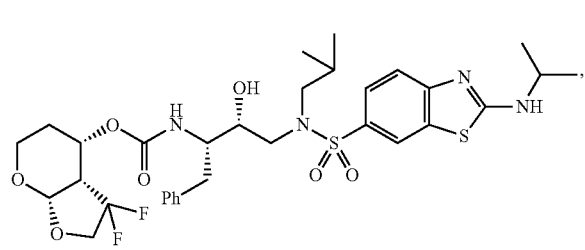

aa.
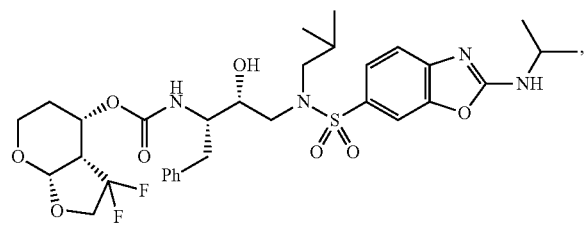

ab.
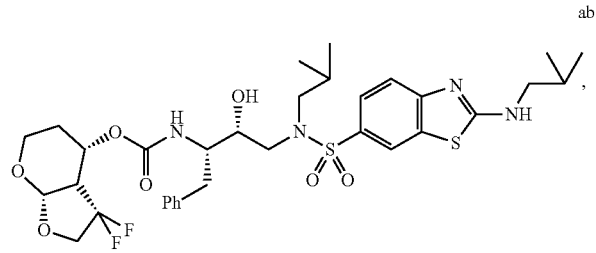

ac.
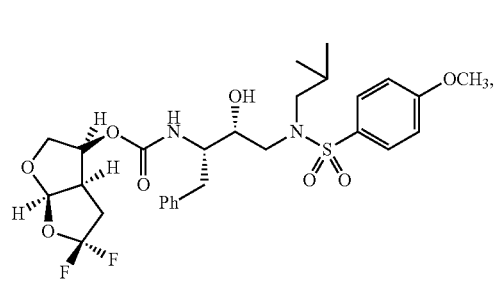

ad.
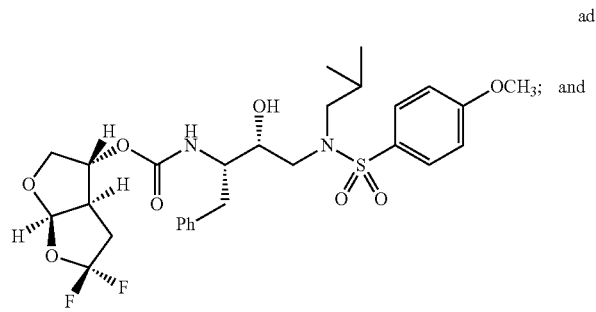

ae.
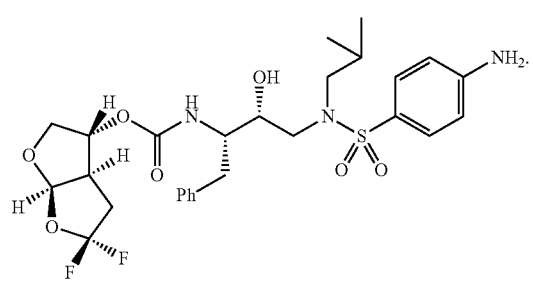

Embodiment 15 relates to the compound of Embodiments 1-14, selected from the group consisting of:

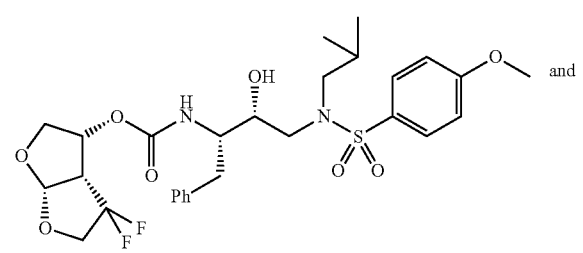 and

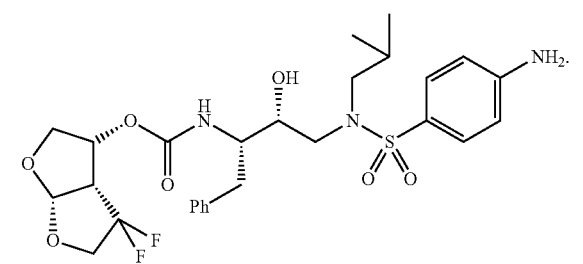

Embodiment 16 relates to a pharmaceutical composition comprising one or more compounds of any one of Embodiments 1-15 and one or more carriers, diluents, or excipients, or a combination thereof.

Embodiment 17 relates to a method for treating a patient in need of relief from an HIV infection, the method comprising the step of administering to a patient in need of relief from the HIV infection a therapeutically effective amount of one or more compounds of any one of Embodiments 1-15.

Embodiment 18 relates to a compound of the formula

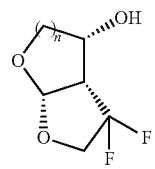

wherein n is the integer 1 or 2.

Embodiment 19 relates to a compound of Embodiment 18 wherein n is the integer 1.

Embodiment 20 relates to the compound of Embodiment 18 wherein n is the integer 2.

What is claimed is:

1. A compound of the formula

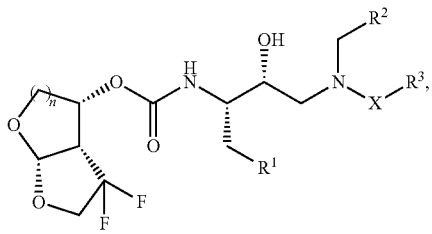

or a pharmaceutically acceptable salt thereof, wherein n is 1;

$R^1$ is phenyl which is unsubstituted or which bears a fluoro, hydroxymethyl, methoxy or 2-(morpholin-4-yl)ethoxy substituent at the 3- or 4-position, or is 3,5-difluorophenyl;

$R^2$ is 2-propyl or 2-fluoro-2-propyl; and

—X—$R^3$ is selected from the group consisting of —$SO_2$—$R^3$, —C(O)—N(R)—$R^3$, —NH—$SO_2$—$R^3$, and —NH—C(O)—$OR^3$;

in which R is selected from the group consisting of (1-6C) alkyl, aryl, heteroaryl, aryl(1-6C)alkyl or heteroaryl(1-6C)alkyl, each of which is optionally substituted; and $R^3$ is selected from the group consisting of (1-6C)alkyl, aryl, heteroaryl, aryl(1-6C)alkyl or heteroaryl(1-6C) alkyl, each of which is optionally substituted.

2. The compound of claim 1 wherein —X—$R^3$ is —$SO_2$—$R^3$.

3. The compound of claim 1, wherein $R^3$ is selected from the group consisting of 4-aminophenyl, 4-methoxyphenyl, 4-hydroxymethylphenyl, 3-fluoro-4-methoxyphenyl, 4-amino-3-fluorophenyl, 3,4-methylenedioxyphenyl, benzoxazole-6-yl bearing a methyl, methylsulfonyl, dimethylamino or —NH—$R^4$ group at the 2-position; benzothiazole-6-yl bearing a methyl, methylsulfonyl, dimethylamino or —NH—$R^4$ group at the 2-position; and
benzimidazole-5-yl bearing a methyl or —NH—$R^4$ group at the 2-position; and
$R^4$ is selected from the group consisting of methyl, prop-2-yl, cyclopropyl, isobutyl, tert-butyl, cyclobutyl, cyclopentyl, cyclohexyl, piperidin-4-yl, 1-methylpiperidin-4-yl, 1-(prop-2-yl) piperidin-4-yl and 1-cyclopentylpiperidin-4-yl.

4. The compound of claim 3, wherein $R^3$ is selected from the group consisting of 4-aminophenyl, 4-methoxyphenyl, and 3-fluoro-4-methoxyphenyl.

5. The compound of claim 3, wherein $R^3$ is 2-(prop-2-ylamino)benzoxazole-6-yl.

6. The compound of claim 3, wherein $R^3$ is benzothiazole-6-yl bearing a methylsulfonyl, dimethylamino, 2-(prop-2-ylamino)-, cyclopropylamino, isobutylamino, tert-butylamino, cyclohexylamino, piperidin-4-ylamino, or 1-cyclopentylpiperidin-4-ylamino group at the 2-position.

7. The compound of claim 1, wherein $R^2$ is 2-propyl.

8. The compound of claim 1, wherein $R^1$ is phenyl, 3-methoxyphenyl or 4-methoxyphenyl.

9. The compound of claim 8 wherein $R^1$ is phenyl.

10. The compound of claim 1, wherein R is hydrogen or methyl.

11. The compound of claim 1, wherein $R^1$ is phenyl, 3-methoxyphenyl or 4-methoxyphenyl; $R^2$ is 2-propyl or 2-fluoro-2-propyl; —X—$R^3$ is —$SO_2$—$R^3$; and $R^3$ is selected from the group consisting of 4-aminophenyl, 4-methoxyphenyl, 3-fluoro-4-methoxyphenyl; 2-(prop-2-ylamino)benzoxazole-6-yl; and benzothiazole-6-yl bearing a methylsulfonyl, dimethylamino, 2-(prop-2-yl-amino)-, cyclopropylamino, isobutylamino, tert-butylamino, cyclohexylamino, piperidin-4-ylamino, or 1-cyclopentylpiperidin-4-ylamino group at the 2-position.

12. The compound of claim 1 selected from the group consisting of:

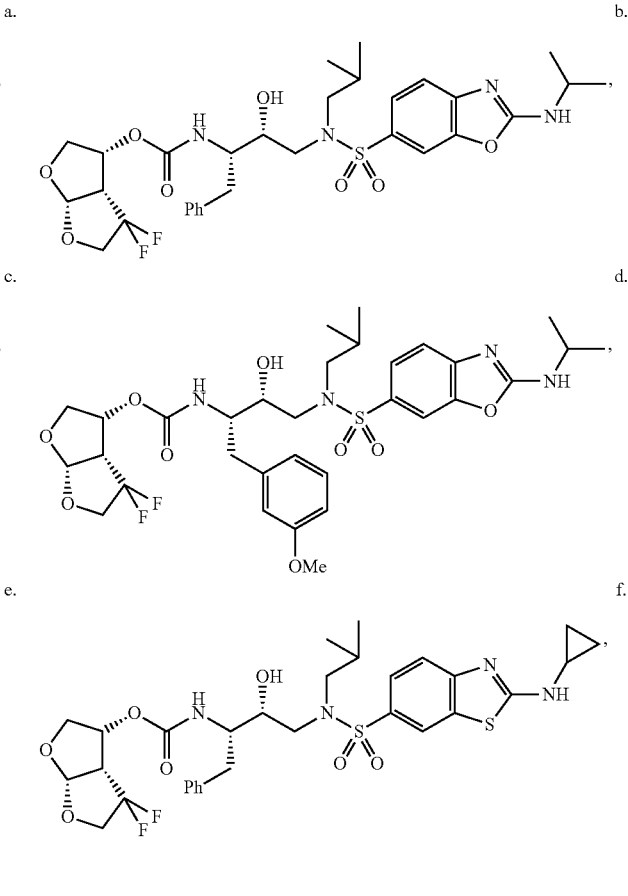

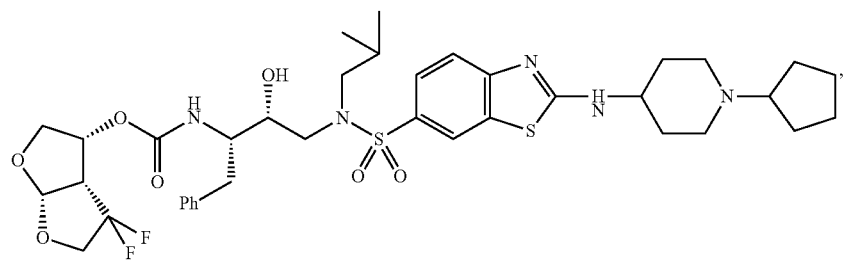

-continued
h.
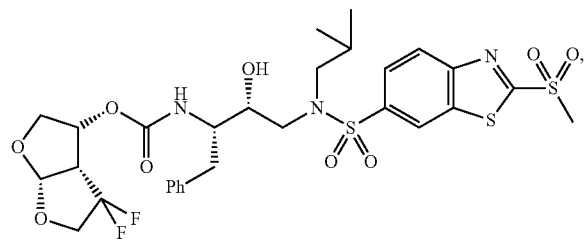
i.
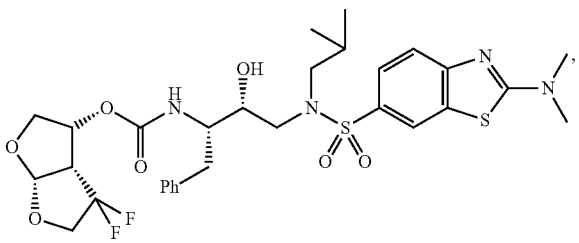
j.
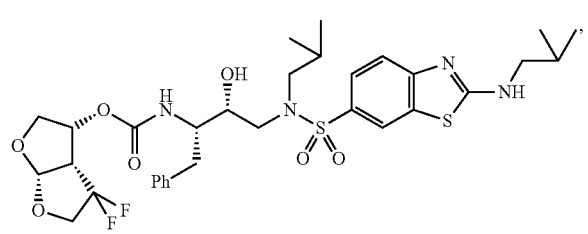
k.
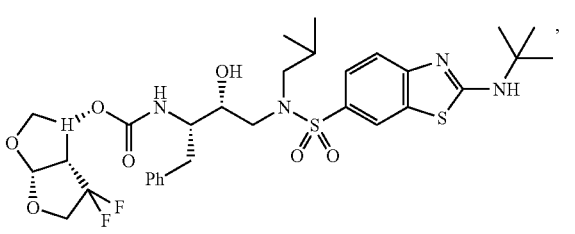
l.
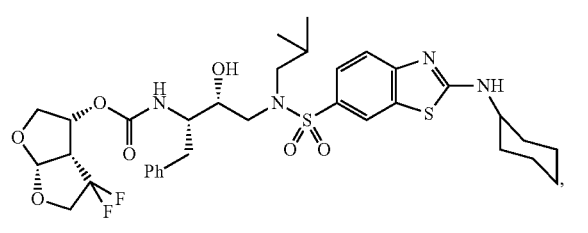
m.
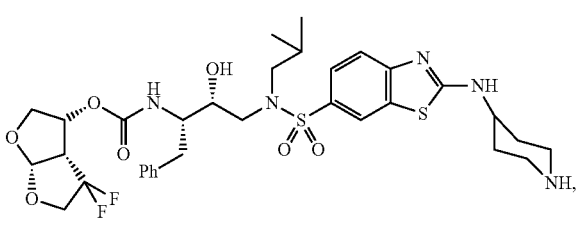
n.
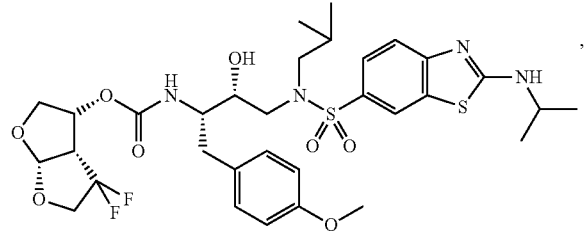
o.
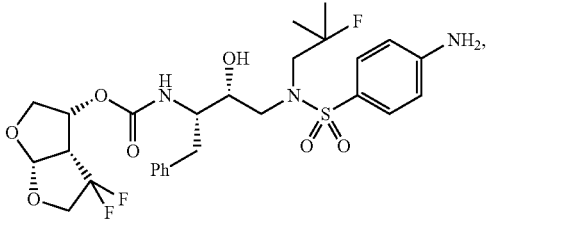
p.
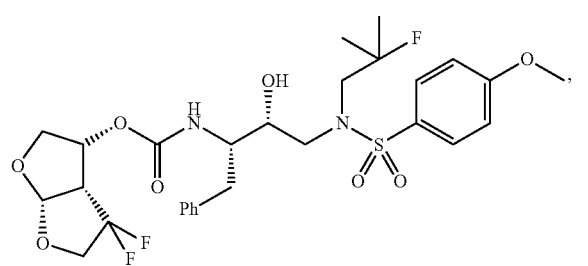
q.
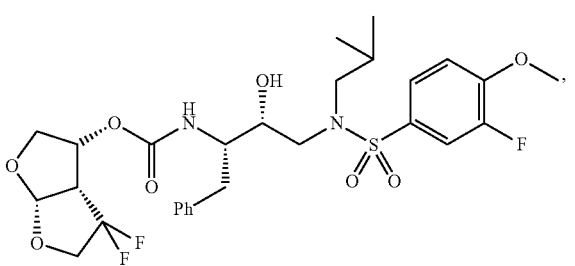
r.
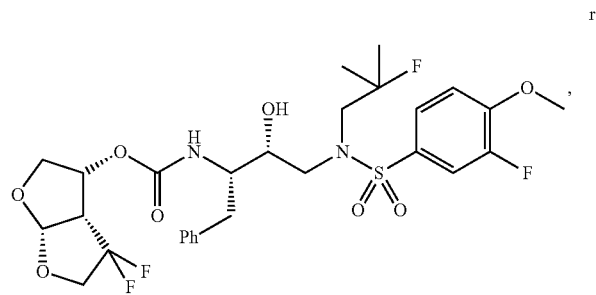
s.
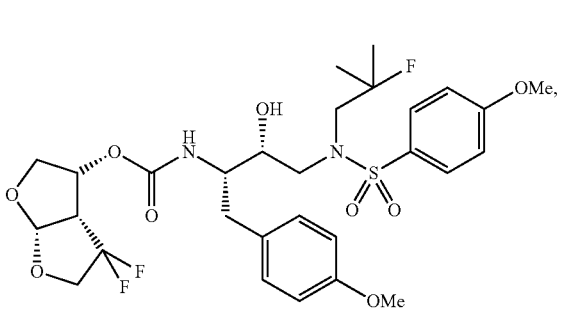

t.
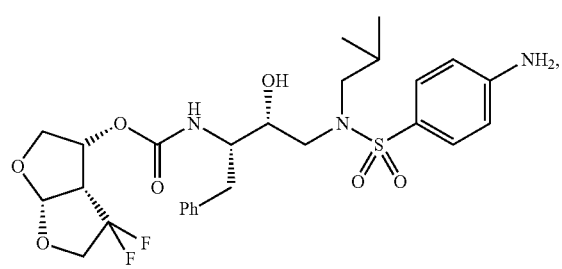
u.
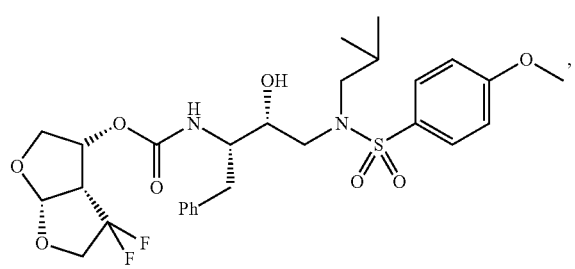
v.
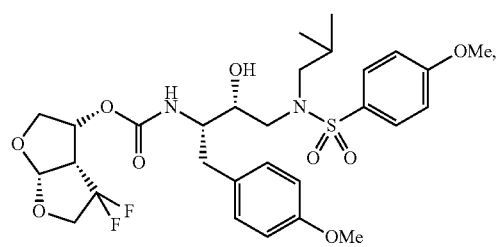
w.
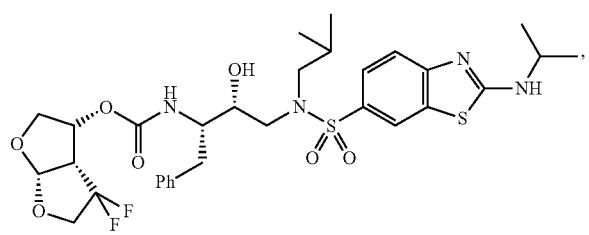
ac.
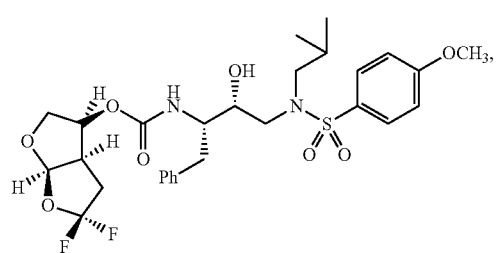
ad.
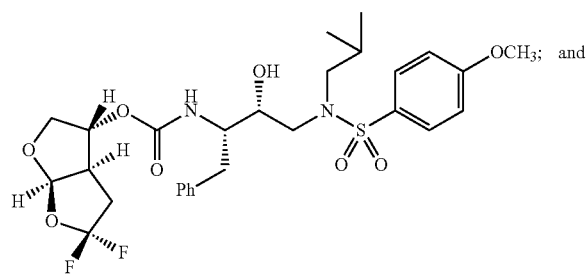
ae.
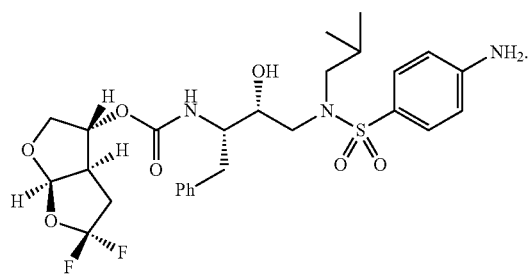
13. The compound of claim 1 selected from the group consisting of:
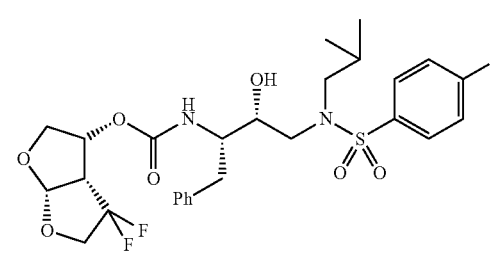 and
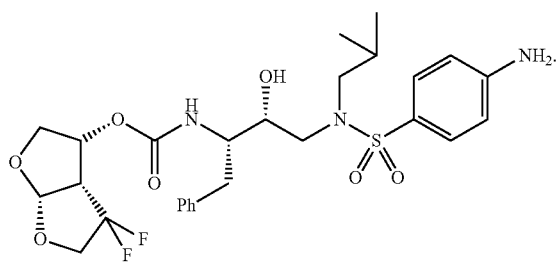

14. A pharmaceutical composition comprising one or more compounds of claim 1 and one or more carriers, diluents, or excipients, or a combination thereof.

15. A method for treating a patient in need of relief from an HIV infection, the method comprising the step of administering to a patient in need of relief from the HIV infection a therapeutically effective amount of one or more compounds of claim 1.

* * * * *

SEQUENCE LISTING

<160> NUMBER OF SEQ ID NOS: 16

<210> SEQ ID NO 1
<211> LENGTH: 99
<212> TYPE: PRT
<213> ORGANISM: HIV-1

<400> SEQUENCE: 1

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 2
<211> LENGTH: 99
<212> TYPE: PRT
<213> ORGANISM: HIV-1

<400> SEQUENCE: 2

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
            20                  25                  30

Phe Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Ile Gly Arg Asn Leu Leu Thr Gln Ile Gly Cys Thr
                85                  90                  95

Leu Asn Phe

<210> SEQ ID NO 3
<211> LENGTH: 99
<212> TYPE: PRT
<213> ORGANISM: HIV-1

<400> SEQUENCE: 3

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ser Asp Asp Thr Val
            20                  25                  30

Phe Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr 65                  70                  75                  80

Pro Ile Asn Ile Ile Gly Arg Asn Leu Leu Thr Gln Ile Gly Cys Thr
                85                  90                  95

Leu Asn Phe

<210> SEQ ID NO 4
<211> LENGTH: 99
<212> TYPE: PRT
<213> ORGANISM: HIV-1

<400> SEQUENCE: 4

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Phe Glu Glu Met Asn Leu Pro Gly Arg Trp Lys Pro Lys Met Ile Gly
                35                  40                  45

Gly Ile Gly Gly Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
65                  70                  75                  80

Pro Ile Asn Ile Ile Gly Arg Asn Leu Leu Thr Gln Ile Gly Arg Thr
                85                  90                  95

Leu Asn Phe

<210> SEQ ID NO 5
<211> LENGTH: 99
<212> TYPE: PRT
<213> ORGANISM: HIV-1

<400> SEQUENCE: 5

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Met Asn Leu Pro Gly Arg Trp Lys Pro Lys Met Ile Gly
                35                  40                  45

Gly Ile Gly Gly Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
65                  70                  75                  80

Pro Ile Asn Ile Ile Gly Arg Asn Leu Leu Thr Gln Ile Gly Cys Thr
                85                  90                  95

Leu Asn Phe

<210> SEQ ID NO 6
<211> LENGTH: 99
<212> TYPE: PRT
<213> ORGANISM: HIV-1

<400> SEQUENCE: 6

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Phe Glu Glu Met Asn Leu Pro Gly Arg Trp Lys Pro Lys Met Ile Gly
                35                  40                  45

Gly Ile Gly Gly Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 7
<211> LENGTH: 99
<212> TYPE: PRT
<213> ORGANISM: HIV-1

<400> SEQUENCE: 7

Pro Gln Ile Thr Leu Trp Gln Arg Pro Leu Val Thr Ile Lys Ile Gly
1               5                   10                  15

Gly Gln Leu Lys Glu Ala Leu Phe Asp Thr Gly Ala Asp Asp Thr Val
            20                  25                  30

Phe Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Ile Gly Arg Asn Leu Leu Thr Gln Ile Gly Cys Thr
                85                  90                  95

Leu Asn Phe

<210> SEQ ID NO 8
<211> LENGTH: 99
<212> TYPE: PRT
<213> ORGANISM: HIV-1

<400> SEQUENCE: 8

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Ile Ile Gly
        35                  40                  45

Gly Val Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 9
<211> LENGTH: 99
<212> TYPE: PRT
<213> ORGANISM: HIV-1

<400> SEQUENCE: 9

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Met Lys Leu Pro Gly Arg Trp Lys Pro Lys Ile Ile Gly
            35                  40                  45

Gly Val Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 10
<211> LENGTH: 99
<212> TYPE: PRT
<213> ORGANISM: HIV-1

<400> SEQUENCE: 10

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Ile Asn Leu Pro Gly Arg Trp Lys Pro Lys Ile Ile Gly
            35                  40                  45

Gly Val Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 11
<211> LENGTH: 99
<212> TYPE: PRT
<213> ORGANISM: HIV-1

<400> SEQUENCE: 11

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Met Asn Leu Pro Gly Arg Trp Lys Pro Lys Ile Ile Gly
            35                  40                  45

Gly Val Gly Gly Phe Ile Lys Ala Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 12
<211> LENGTH: 99
<212> TYPE: PRT
<213> ORGANISM: HIV-1

```
<400> SEQUENCE: 12

Pro Gln Ile Thr Leu Trp Gln Arg Pro Leu Val Thr Ile Lys Ile Gly
1               5                   10                  15

Val Gln Leu Lys Glu Ala Leu Leu Asp Thr Gly Ala Asp Asp Thr Val
                20                  25                  30

Leu Glu Glu Met Asn Leu Pro Gly Arg Trp Lys Pro Lys Ile Ile Gly
            35                  40                  45

Gly Val Gly Gly Phe Ile Lys Val Arg Gln Tyr Asp Gln Ile Leu Ile
50                  55                      60

Glu Ile Cys Gly His Lys Ala Ile Gly Thr Val Leu Val Gly Pro Thr
65              70                  75                  80

Pro Val Asn Ile Ile Gly Arg Asn Leu Leu Thr Gln Ile Gly Cys Thr
                85                  90                  95

Leu Asn Phe

<210> SEQ ID NO 13
<211> LENGTH: 22
<212> TYPE: DNA
<213> ORGANISM: HIV-1

<400> SEQUENCE: 13
gatgctacat ataagcagct gc                                        22

<210> SEQ ID NO 14
<211> LENGTH: 24
<212> TYPE: DNA
<213> ORGANISM: HIV-1

<400> SEQUENCE: 14
ctcgtgacaa atttctacta atgc                                      24

<210> SEQ ID NO 15
<211> LENGTH: 22
<212> TYPE: DNA
<213> ORGANISM: HIV-1

<400> SEQUENCE: 15
gagactctgg taactagaga tc                                        22

<210> SEQ ID NO 16
<211> LENGTH: 28
<212> TYPE: DNA
<213> ORGANISM: HIV-1

<400> SEQUENCE: 16
ccatcccggg ctttaatttt actggtac                                  28
```